US008367609B2

(12) United States Patent
Detmar et al.

(10) Patent No.: US 8,367,609 B2
(45) Date of Patent: Feb. 5, 2013

(54) METHODS OF REDUCING SKIN DAMAGE AND EDEMA

(75) Inventors: Michael Detmar, Boppelsen (CH); Kentaro Kajiya, Schweiz (CH)

(73) Assignee: The General Hospital Corporation, Boston, MA (US)

( * ) Notice: Subject to any disclaimer, the term of this patent is extended or adjusted under 35 U.S.C. 154(b) by 226 days.

(21) Appl. No.: 11/654,776

(22) Filed: Jan. 18, 2007

(65) Prior Publication Data

US 2007/0224137 A1  Sep. 27, 2007

Related U.S. Application Data

(60) Provisional application No. 60/760,328, filed on Jan. 18, 2006.

(51) Int. Cl.
*A61K 38/18* (2006.01)

(52) U.S. Cl. ........ 514/8.1; 514/9.4; 514/12.2; 514/18.6; 514/18.7

(58) Field of Classification Search .................. None
See application file for complete search history.

(56) References Cited

U.S. PATENT DOCUMENTS

| | | | |
|---|---|---|---|
| 6,001,885 A | 12/1999 | Vega et al. | |
| 6,018,098 A * | 1/2000 | Bernstein et al. | 623/16.11 |
| 6,093,740 A * | 7/2000 | Jirousek et al. | 514/414 |
| 6,235,713 B1 | 5/2001 | Achen et al. | |
| 6,337,320 B1 * | 1/2002 | Hersh et al. | 514/18 |
| 6,383,484 B1 * | 5/2002 | Achen et al. | 424/133.1 |
| 6,712,617 B2 | 3/2004 | Detmar et al. | |
| 6,824,777 B1 | 11/2004 | Alitalo et al. | |
| 6,867,348 B1 * | 3/2005 | Zhang et al. | 800/18 |
| 7,534,572 B2 * | 5/2009 | Achen et al. | 435/7.1 |
| 7,556,809 B2 * | 7/2009 | Romero et al. | 424/185.1 |
| 7,727,761 B2 * | 6/2010 | Alitalo et al. | 435/375 |
| 7,829,536 B2 * | 11/2010 | Ferrell et al. | 514/1.1 |
| 2002/0119921 A1 * | 8/2002 | Streit et al. | 514/12 |
| 2003/0008821 A1 | 1/2003 | Detmar et al. | |
| 2004/0208879 A1 | 10/2004 | Alitalo et al. | |
| 2005/0071016 A1 * | 3/2005 | Hausdorf et al. | 623/23.75 |
| 2005/0281761 A1 | 12/2005 | Detmar et al. | |

FOREIGN PATENT DOCUMENTS

| | | |
|---|---|---|
| WO | WO 98/07832 | 2/1998 |
| WO | WO 2002/083088 | 10/2002 |
| WO | WO 2005/097187 | 10/2005 |

OTHER PUBLICATIONS

Kaner et al. Am. J. Respir. Cell Mol. Biol. 22:657-664, 2000.*
Larcher et al. Oncogene 17:303-311, 1998.*
Blaudschun et al., "Vascular endothelial growth factor causally contributes to the angiogenic response upon ultraviolet B irradiation in vivo," Br. J. Dermatol., 146:581-587 (2002).
Doll et al., "Thrombospondin-1, Vascular Endothelial Growth Factor and Fibroblast Growth Factor-2 Are Key Functional Regulators of Angiogenesis in the Prostate," Prostate, 49:293-305 (2001).
Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types," Cancer Res., 59:99-106 (1999).
Giles, F, "The Vascular Endothelial Growth Factor (VEGF) Signaling Pathway: A Therapeutic Target in Patients with Hematologic Malignancies," Oncologist, 6(Suppl. 5):32-39 (2001).
Gupta et al., "Binding and displacement of vascular endothelial growth factor (VEGF) by thrombospondin: Effect on human microvascular endothelial cell proliferation and angiogenesis," Angiogenesis, 3:147-158 (2000).
Toi et al., "Preliminary studies on the anti-angiogenic potential of pomegranate fractions in vitro and in vivo," Angiogenesis, 6:121-128 (2003).
Witte et al., "Monoclonal antibodies targeting the VEGF receptor-2 (Flk1/KDR) as an anti-angiogenic therapeutic strategy," Cancer Metastasis Rev., 17:155-161 (1998).
Byrne et al., "Angiogenic and Cell Survival Functions of Vascular Endothelial Growth Factor (VEGF)", J. Cell. Molec. Med., 9:777-794, (2005).
Coultas et al., "Endothelial Cells and VEGF in Vascular Development", Nature, 438:937-945 (2005).
Detmar et al., "Increased Microvascular Density and Enhanced Leukocyte Rolling and Adhesion in the Skin of VEGF Transgenic Mice", J. Invest. Derm. 111:1-6 (1998).
Goldman et al., "Overexpression of VEGF-C causes transient lymphatic hyperplasia but not increased lymphangiogenesis in regenerating skin", Circulation Research, 96:1193-1199, (2005).
Hirakawa et al., "Vascular endothelial growth factor promotes sensitivity to ultraviolet B-induced cutaneous photodamage", Blood, 105:2392-2399, (2005).
Hirakawa et al., "VEGF-A Induces Tumor and Sentinel Lymph Node Lymphangiogenesis and Promotes Lymphatic Metastasis", J. Exp. Med., 201:1089-1099, (2005).
Jussila et al., "Vascular Growth Factors and Lymphangiogenesis", Physiol. Rev., 82:673-700, (2002).
Kajiya et al., "An Important Role of Lymphatic Vessels in the Control of UVB-Induced Edema Formation and Inflammation", J. Invest. Dermatol., 126:920-922, (2006).
Kajiya et al., "Vascular endothelial growth factor-A mediates ultraviolet B-induced impairment of lymphatic vessel function", American Journal of Pathology, 169:1496-1503, (2006).
Kunstfeld et al., "Induction of Cutaneous Delayed-Type Hypersensitivity Reaction in VEGF-A Transgenic Mice Results in Chronic Skin Inflammation Associated with Persistent Lymphatic Hyperplasia", Blood, 104:1048-1057, (2004).
Levine et al., "Phase I trial of vascular endothelial growth factor-antisense (VEGF-AS, Veglin) in relapsed and refractory malignancies", Blood, 102:123A, (2003).
Liu et al., "Upregulation of neuropilin-1 by basic fibroblast growth factor enhances vascular smooth muscle cell migration in response to VEGF", Cytokine, 32:206-212, (2005).

(Continued)

*Primary Examiner* — Christine J Saoud
(74) *Attorney, Agent, or Firm* — Fish & Richardson P.C.

(57) ABSTRACT

This application features methods of treating (e.g., reducing, ameliorating, or preventing) skin damage (e.g., induced by UVB) by decreasing the level or activity of VEGF-A, e.g., in the skin, of a subject.

20 Claims, 6 Drawing Sheets

OTHER PUBLICATIONS

Nagy et al., "Vascular Permeability Factor/Vascular Endothelial Growth Factor Induces Lymphangiogenesis as well as Angiogenesis", J. Exp. Med., 196:1497-1506, (2002).

Oliver et al., "The Rediscovery of the Lymphatic System: Old and New Insights into the Development and biological Function of the Lymphatic Vasculature", Genes Dev., 16:773-783, (2002).

Rodriguez et al., "Epigallocatechin-gallate (EGCG) inhibits VEGF-induced angiogensis by suppressing receptor complex formation, PI3-kinase activity and production of IL-8 via NF-kB pathway", FASEB J., 18:A270.5, (2004).

Shibuya et al., "Signal Transduction by VEGF receptors in Regulation of Angiogenesis and Lymphangiogenesis", Exp. Cell Res., 312:549-560, (2006).

Witte et al., "Lymphangiogenesis and Lymphangiodysplasia: From Molecular to Clinical Lymphology", Microscopy Res. Tech., 55:122-145, (2001).

Yano et al., "Ultraviolet B-Induced Skin Angiogenesis is Associated with a Switch in the Balance of Vascular Endothelial Growth Factor and Thrombospondin-1 Expression", J. Invest. Dermatol., 122:201-208, (2004).

Yano et al., "Ultraviolet B Irradiation of Human Skin Induces an Angiogenic Switch That Is Mediated by Upregulation of Vascular Endothelial Growth Factor and by Downregulation of Thrombospondin-1", British J. Dermotology, 152:115-121, (2005).

Achen et al., "Vascular endothelial growth factor D (VEGF-D) is a ligand for the tyrosine kinases VEGF receptor 2 (Flk1) and VEGF receptor 3 (Flt4)," Proc. Natl. Acad. Sci. USA, 95:548-553 (1998).

Joukov et al., "A recombinant mutant vascular endothelial growth factor-C that has lost vascular endothelial growth factor receptor-2 binding, activation, and vascular permeability activities," J. Biol. Chem., 273:6599-6602 (1998).

Lee et al., "Vascular endothelial growth factor-related protein: a ligand and specific activator of the tyrosine kinase receptor Flt4," Proc. Natl. Acad. Sci. USA, 93:1988-92 (1996).

Kajiya et al., "Activation of the VEGFR-3 Pathway by VEGF-C Attenuates UVB-Induced Edema Formation and Skin Inflammation by Promoting Lymphangiogenesis," *J. Invest. Dermatol.* 129:1292-1298, 2009.

Malaviya et al., "Anti-Inflammatory Activity of 2,4,6-Trihydroxy-α-p-Methoxyphenyl-acetophenone (Compound D-58)," *Dermatology* 201:337-342, 2000.

Reagan-Shaw et al., "Modulations of Critical Cell Cycle Regulatory Events During Chemoprevention of Ultraviolet B-Mediated Responses by Resveratrol in SKH-1 Hairless Mouse Skin," *Oncogene* 23:5151-5160, 2004.

European Search Report for European Application No. 10172193.4, dated Feb. 17, 2011.

Alitalo et al., "Lymphangiogenesis in development and human disease," Nature, 438:946-953 (2005).

Baluk et al., "Pathogenesis of persistent lymphatic vessel hyperplasia in chronic airway inflammation," J. Clin. Invest., 115:245-257 (2005).

Cao, "Opinion: emerging mechanisms of tumour lymphangiogenesis and lymphatic metastasis," Nat. Rev. Cancer, 5:735-743 (2005).

Cueni and Detmar, "New insights into the molecular control of the lymphatic vascular system and its role in disease," J. Invest. Dermatol., 126:2167-77 (2006).

Dvorak, "Angiogenesis: update 2005," J. Thromb. Haemost., 3:1835-42 (2005).

Jeltsch et al., "Hyperplasia of lymphatic vessels in VEGF-C transgenic mice," Science, 276:1423-25 (1997).

Joukov et al., "Proteolytic processing regulates receptor specificity and activity of VEGF-C," EMBO J., 16:3898-3911 (1997).

Joukov et al., "A novel vascular endothelial growth factor, VEGF-C, is a ligand for the Flt4 (VEGFR-3) and KDR (VEGFR-2) receptor tyrosine kinases," EMBO J., 15:1751 (1996).

Jurisic and Detmar, "Lymphatic endothelium in health and disease," Cell Tissue Res., 335:97-108 (2008).

Kajiya et al., "Reduction of lymphatic vessels in photodamaged human skin," J. Dermatol. Sci., 47:241-243 (2007).

Mäkinen et al., "Inhibition of lymphangiogenesis with resulting lymphedema in transgenic mice expressing soluble VEGF receptor-3," Nat. Med., 7:199-205 (2001).

Oliver and Alitalo, "The lymphatic vasculature: recent progress and paradigms," Annu. Rev. Cell Dev. Biol., 21:457-483 (2005).

Saaristo et al., "Vascular endothelial growth factor-C gene therapy restores lymphatic flow across incision wounds," FASEB J., 18:1707-09 (2004).

Skobe and Detmar, "Structure, function, and molecular control of the skin lymphatic system," J. Investig. Dermatol. Symp. Proc., 5:14-19 (2000).

Tobler and Detmar, "Tumor and lymph node lymphangiogenesis—impact on cancer metastasis," J. Leukoc. Biol., 80:691-696 (2006).

Veikkola et al., "Signalling via vascular endothelial growth factor receptor-3 is sufficient for lymphangiogenesis in transgenic mice," EMBO J., 20:1223-31 (2001).

Guo-rong et al., "Research on the protection for ultraviolet radiation of sun light on skin," China Surfactant Detergent & Cosmetics, 32(1):55-58 (2002) with translation.

Detmar, Michael, "The role of VEGF and thrombospondins in skin angiogenesis," Journal of Dermatological Science, 24(Suppl ):S78-S84 (2000).

Office Action issued in Chinese Application No. 200780009605.5 on Jun. 4, 2012 (4 pages).

* cited by examiner

METHODS OF REDUCING SKIN DAMAGE AND EDEMA

CROSS-REFERENCE TO RELATED APPLICATIONS

This application claims priority to U.S. Application Ser. No. 60/760,328, filed on Jan. 18, 2006, which is incorporated herein by reference in its entirety.

GOVERNMENT SUPPORT

This invention was made with Government support under Grant No. CA069184 awarded by the National Institutes of Health. The Government has certain rights in this invention.

BACKGROUND

The lymphatic vascular system is composed of a dense network of thin-walled capillaries that drain protein-rich lymph from the extracellular space. Its major roles include the maintenance of tissue fluid homeostasis and mediation of the afferent immune response (Oliver et al. (2002) Genes Dev. 16:773-83; Witte et al. (2001) Microsc. Res. Tech. 55:122-45). One known function of lymphatic vessels is the drainage of tissue fluid from normal and inflamed tissues (Kunstfeld et al. (2004) Blood 104:1048-57).

SUMMARY

We report that both acute and chronic UVB-irradiation of murine skin results in prominent enlargement of lymphatic vessels. Surprisingly, these enlarged lymphatic vessels are functionally impaired and are hyperpermeable, as detected by intravital lymphangiography. The expression levels of vascular endothelial growth factor (VEGF)-A, but not of the known lymphangiogenesis factors VEGF-C or -D were enhanced in UVB-irradiated epidermis. Targeted overexpression of VEGF-A in the epidermis of transgenic mice led to increased enlargement and leakage of lymphatic vessels after acute UVB irradiation, whereas systemic blockade of VEGF-A signaling largely prevented lymphatic vessel abnormalities and photo-damage induced by UVB. Together, these findings indicate that lymphatic vessels are targets for UVB-induced cutaneous photodamage, and that VEGF-A mediates impairment of lymphatic vessel function and thereby contributes to the adverse effects of UVB irradiation on the skin.

In one aspect, the disclosure features methods of reducing UVB induced skin damage by decreasing the activity or levels of VEGF-A in the skin, e.g., on the face, chest, neck, hands, or other regions of the body. These methods can further include increasing the activity or levels of a lymphangiogenic factor, e.g., VEGF-C or VEGF-D, in the skin.

In another aspect, the disclosure features methods of reducing edema by decreasing the activity or levels of VEGF-A.

In still another aspect, the disclosure features methods of reducing UVB induced skin damage, e.g., on the face, chest, neck, hands, or other regions of the body, by promoting lymphatic function.

In yet another aspect, the disclosure features methods of screening for an inhibitor of VEGF-A activity by providing cell with transmembrane receptor that can bind and respond to VEGF-A; contacting the cell with a polypeptide that includes VEGF-A or a fragment thereof in the presence of a test compound, e.g., a natural product or extract; and evaluating binding of the polypeptide to the cell, wherein a test compound that inhibits binding of the polypeptide to the cell is an inhibitor of VEGF-A activity.

In yet another aspect, the disclosure features methods of screening for an inhibitor of VEGF-A activity by providing a first polypeptide that includes a portion of a transmembrane receptor that can bind to VEGF-A; contacting the polypeptide with a second polypeptide that includes VEGF-A or a fragment thereof in the presence of a test compound, e.g., a natural product or extract; and evaluating binding of the first polypeptide to the second polypeptide, wherein a test compound that inhibits binding of the first polypeptide to the second polypeptide is an inhibitor of VEGF-A activity.

In still another aspect, of screening for an inhibitor of VEGF-A expression, the method comprising: (a) providing a cell having a VEGF-A promoter region; (b) exposing the cell to UVB radiation; (c) before, during, or after b), contacting the cell with a test compound, e.g., a natural product or extract; and (d) measuring expression directed by the promoter region, wherein a test compound that decreases expression is an inhibitor of VEGF-A expression.

In one aspect, the disclosure features a method of treating a subject having UVB-induced skin damage, e.g., on the face, chest, neck, hands, or other regions of the body. The method includes administering, to the subject, a therapeutically effective amount of a VEGF/VEGFR modulator.

In one embodiment, the modulator is a VEGF-A/VEGFR (e.g., VEGFR-2) antagonist. A VEGF-A/VEGFR antagonist is an agent that directly or indirectly decreases VEGF-A/VEGFR activity in a cell or in the subject. Antagonists include nucleic acids and proteins, e.g., antibodies or soluble VEGF-A receptor fragments. For example, the antagonist can be a protein that interacts with VEGF-A and, e.g., reduces VEGF-A binding affinity to cell surface VEGFR (e.g., VEGFR-2). For example, the protein can be (i) an antibody that recognizes VEGF-A or VEGFR (e.g., VEGFR-2), or (ii) a protein that includes a extracellular region of the VEGFR, e.g., a soluble VEGF-A receptor (e.g., fused to an Fc domain). Examples of antagonists include: a nucleic acid molecule that can bind or otherwise inhibit VEGF-A mRNA, e.g., mRNA production, processing, or translation. Still other antagonists include: a dominant negative VEGF-A protein or fragment thereof and an agent which decreases VEGF-A nucleic acid expression (e.g., an artificial transcription factor or nucleic acid encoding an artificial transcription factor). Other suitable VEGF-A/VEGFR (e.g., VEGFR-2) antagonists include small molecules, natural products, and extracts.

In some implementations, the modulator decreases the endogenous level of VEGF-A or VEGFR (e.g., VEGFR-2).

In one embodiment the modulator is a VEGF-C/D/VEGFR (e.g., VEGFR-3) agonist. A VEGF-C/D/VEGFR agonist is an agent that directly or indirectly increases VEGF-C/D/VEGFR activity in the subject.

Many VEGF-C/D/VEGFR (e.g., VEGFR-3) agonists increase VEGFR signaling activity. Examples of VEGF-C/D/VEGFR agonists include a protein that includes a VEGF-C/D polypeptide (e.g., as modified into its mature heterodimeric form) or a biologically active fragment or analog thereof, a nucleic acid encoding a VEGF-C/D or a biologically active fragment or analog thereof. Other proteins and molecules, e.g., antibodies and small molecules, can also be used increase VEGFR activity. For example, antibodies that bind, and optionally crosslink (e.g., dimerize) VEGFR (e.g., VEGFR-3) can be used to VEGFR (e.g., VEGFR-3) activity. Other suitable VEGF-C/D/VEGFR (e.g., VEGFR-3) agonists include small molecules, natural products, and extracts.

The modulators can be used to treat a condition in which increased lymphatic vessel function is desired. Such conditions included edema, e.g., due to UVB irradiation. Other conditions in which increased lymphatic vessel function is desired include aged skin or damaged skin, e.g., UVB-damaged skin. Still other conditions include those caused in part by a genetic or environmental factor, e.g., ultraviolet radiation. For example, the condition is skin extracellular matrix damage, e.g., caused by aging or excessive exposure to ultraviolet light.

In another aspect, the disclosure features a method of identifying a compound that modulates lymphatic function. The method includes: providing a cell or organism in which VEGF-A/VEGFR (e.g., VEGFR-2) activity can be monitored; contacting the cell or organism with a test compound, e.g., a natural product or extract, and evaluating VEGF-A/VEGFR (e.g., VEGFR-2) activity in the cell or organism. For example, the cell includes a reporter of VEGF-A/VEGFR (e.g., VEGFR-2) activity or an organism that comprises such a cell. VEGF-A/VEGFR activity can be evaluated by evaluating, e.g., protein or mRNA expression or reporter activity. A change in reporter activity or other relevant parameter, for example, indicates a change in VEGF-A/VEGFR activity. The method can further include evaluating the effect of the test compound on cell proliferation or cell migration, e.g., lymphatic endothelial cell proliferation or migration.

In one embodiment, the reporter is a gene that comprises a sequence encoding a detectable protein and an operably linked promoter that includes a region of the promoter of the VEGF-A or VEGFR (e.g., VEGFR-2) gene, e.g. region from the transcription start site to a position at least 100, 200, 300, 500, 800, 1000, 2000, or 5000 bases upstream, from the initiator MET codon to a position at least 100, 200, 300, 500, 800, 1000, 2000, or 5000 bases upstream, or from the TATA box to a position at least 100, 200, 300, 500, 800, 1000, 2000, or 5000 bases upstream.

The cell or organism is generally mammalian, e.g., human or non-human, e.g., a mouse, rat, hamster, guinea pig, monkey and so forth.

In still another aspect, the disclosure features a method for evaluating a test compound, e.g., a compound (e.g., a natural product or extract) that is topically applied to a test organism, e.g., a transgenic organism that includes a reporter of VEGF-A/VEGFR (e.g., VEGFR-2) pathway activity. The method includes contacting a test compound to the test organism and evaluating VEGF-A/VEGFR pathway activity. For example, the evaluating can include evaluating protein or mRNA expression of VEGF-A, VEGFR (e.g., VEGFR-2), or a gene or gene product that is regulated by VEGFR. The method can also include evaluating the test compound in the presence of another VEGF-A/VEGFR pathway modulator, e.g., in the presence of a protein that includes soluble VEGF, a protein that includes a soluble extracellular domain of VEGFR, or antibody to VEGF-A or VEGFR.

In one embodiment, the reporter is a gene that includes a sequence encoding a detectable protein and an operably linked promoter that includes a region of the promoter of the VEGF, or VEGFR gene, e.g. region from the transcription start site to a position at least 100, 200, 300, 500, 800, 1000, 2000, or 5000 bases upstream, from the initiator MET codon to a position at least 100, 200, 300, 500, 800, 1000, 2000, or 5000 bases upstream, or from the TATA box to a position at least 100, 200, 300, 500, 800, 1000, 2000, or 5000 bases upstream. The method can also include evaluating two or more such reporters.

The method can include selecting a test compound (e.g., from a library of test compounds, e.g., of natural products or extracts), if it alters, e.g., (increases or decreases) VEGF/VEGFR pathway activity. A selected test compound can be formulated, e.g., as a pharmaceutical composition, e.g., suitable for topical administration or other route of administration. The method can further include administering the pharmaceutical composition to a subject, e.g., a subject having or at risk for a disorder described herein.

In one aspect, the invention features a method for identifying an agent that modulates, e.g., reduces, skin damage, e.g., radiation induced skin damage such as chronic or acute UVB-induced skin damage. The method includes identifying an agent, (e.g., a natural product or extract) that modulates, e.g., decreases, VEGF-A signaling (e.g., an agent that the reduces the expression, activity or levels of VEGF-A or of a VEGF receptor (VEGFR, (e.g., VEGFR-2)), and correlating the ability of an agent to modulate VEGF-A signaling, levels or activity with the ability to modulate skin damage, e.g., radiation induced skin damage such as chronic or acute UVB-induced skin damage. The method can further include selecting an identified agent, e.g., an agent that modulates skin damage.

In one embodiment, the agent is identified by evaluating the ability of a test agent to interact with, e.g., to bind, VEGF-A or VEGFR (e.g., VEGFR-2). In another embodiment, the agent is identified by evaluating the effect of a test agent to interact with a VEGF-A or VEGFR regulatory region, e.g., a promoter, e.g., a VEGF-A or a VEGFR promoter. In another embodiment, the agent is identified by evaluating the effect of the test agent on VEGF-A production in a skin cell, e.g., a keratinocyte. In another embodiment, the agent is identified by evaluating, e.g., quantitatively or qualitatively evaluating, the ability of a test agent to modulate acute VEGF-A signaling in a whole animal model, e.g., in a VEGF-A transgenic animal such as a VEGF-A overexpressing animal.

The test agent can be, e.g., a nucleic acid (e.g., an antisense, ribozyme), a polypeptide (e.g., an antibody or antigen-binding fragment thereof), a peptide fragment, a peptidomimetic, or a small molecule (e.g., a small organic molecule with a molecular weight of less than 2000 daltons). The test agent can be evaluated in a purified form, e.g., at least 10, 50, 70, 80, 90, or 99% pure, e.g., in a homogenous composition that does not include other test agents. In another preferred embodiment, the test agent is a member of a combinatorial library, e.g., a peptide or organic combinatorial library, or a natural product or extract library. In a preferred embodiment, a plurality of test agents, e.g., library members, is tested. Preferably, the test agents of the plurality, e.g., library, share structural or functional characteristics. The test agent can also be a crude or semi-purified extract, e.g., a botanical extract such as a plant extract, or algal extract.

The method can include comparing, correlating, or associating the effect of the agent on VEGF-A or VEGFR (e.g., VEGFR-2) expression, levels, or activity, with a predicted effect of the agent on a mammal, e.g., a human, e.g., by providing (e.g., to the government, a health care provider, insurance company or patient) informational, marketing or instructional material, e.g., print material or computer readable material (e.g., a label, an email), related to the agent or its use, identifying the effect of the agent as a possible or predicted effect of the agent in a mammal, e.g., a human. E.g., the method can include identifying the agent as an agent that reduces acute UVB-induced skin damage, e.g., in humans, if it decreases VEGF-A or VEGFR (e.g., VEGFR-2) expression, levels or activity, compared to a reference. The identification can be in the form of informational, marketing or instructional material, e.g., as described herein. In one embodiment, the method includes correlating a value for the effect of the agent with ability to reduce skin damage, e.g., generating a dataset correlating a value for the effect of the agent with ability to reduce skin damage.

In one embodiment, the method includes at least two evaluating steps, e.g., the method includes a first step of evaluating the test agent in a first system, e.g., a cell-free, cell-based, tissue system or animal model, and a second step of evaluating the test agent in a second system, e.g., a second cell or tissue system or in a non-human animal. In one embodiment, one of the evaluating steps includes evaluating the effect of the agent on a subject's skin or skin explant, e.g., evaluating the presence, extent or type of skin damage in the skin, preferably before and after acute UVB exposure. The subject can be an experimental animal or a human. In one embodiment, the first evaluation includes testing the effect of the test agent on a VEGF-A or VEGFR (e.g., VEGFR-2) promoter that is linked to a heterologous sequence such as a reporter gene, and the second evaluation includes administering the test agent to a system, e.g., a cell based or animal system and evaluating effect of the agent on skin damage and/or VEGF production. In some embodiments, the method includes two evaluating steps in the same type of system, e.g., the agent is re-evaluated in a non-human animal after a first evaluation in the same or a different non-human animal. The two evaluations can be separated by any length of time, e.g., days, weeks, months or years.

In a preferred embodiment, the identifying step includes: (a) providing an agent to a cell, tissue or non-human animal whose genome includes an exogenous nucleic acid that includes a regulatory region of a VEGF-A or VEGFR (e.g., VEGFR-2) gene (see, e.g., Gille et al., EMBO J. 1997 vol. 16(4):750-9 for VEGF-A promoter; and Giraudo et al., J Biol Chem. 1998 vol. 273(34):22128-35 for VEGFR-2 (flk1) promoter), operably linked to a heterologous sequence, e.g., a nucleotide sequence encoding a reporter polypeptide (e.g., a colorimetric (e.g., LacZ), luminometric, e.g., luciferase, or fluorescently detectable reporter polypeptide, e.g. GFP, EGFP, BFP, RFP); (b) evaluating the ability of a test agent to modulate the expression of the reporter polypeptide in the cell, tissue or non-human animal; and (c) selecting a test agent that modulates the expression of the reporter polypeptide as an agent that modulates acute UVB-induced skin damage.

In one embodiment, the animal is an experimental rodent. The animal can be wild type or a transgenic experimental animal, e.g., a VEGF-A transgenic rodent, e.g., a VEGF transgenic mouse. The subject can also be a human. In a preferred embodiment, the evaluating step comprises administering the agent to the subject and evaluating skin damage (e.g., skin damage caused by acute exposure to UVB). In another embodiment, the cell or tissue is a skin cell, e.g., a keratinocyte; or tissue, e.g., a skin explant. In yet another embodiment, a cell, e.g., a skin cell, e.g., a keratinocyte, or a tissue, e.g., a skin explant, is derived from a transgenic animal.

In another aspect, the invention features a method of treating a subject, e.g., a human subject. The method includes (a) identifying a subject at risk for, or having, edema or skin damage, e.g., due to radiation exposure, e.g., chronic or acute UVB-exposure; and (b) administering to the subject an agent (e.g., a natural product or extract) that modulates VEGF-A signaling in the subject, e.g., administering to the subject an effective amount of an agent that decreases the activity, level or expression of VEGF-A or VEGFR (e.g., VEGFR-2), e.g., an agent described herein. Preferably, the agent is administered to the subject's skin, e.g., topically. In a preferred embodiment, chronic or acute UVB-induced redness, inflammation, edema, blistering, swelling and/or sunburn of the skin are prevented or reduced. Acute UVB-exposure means exposure to at least one MED of UVB light, preferably at least 2, 3, or 5 MEDS. In one embodiment, the subject is exposed to between 3-8 MEDS, e.g., 3-5, 5-7, or 7-8 MEDS. In some embodiments, the subject will be, is, or has been, exposed to the sun when the UV index is moderate to extreme, e.g., for a time sufficient to cause sunburn. The subject may exhibit one or more symptom of acute UVB exposure, e.g., skin inflammation, redness, swelling, blistering, tenderness or edema. Typically, the subject is at least 5 years of age. Preferably, the subject is at least 10, 15, 20, 25, 30, 35, 40, 45, 50, or more years of age.

In a preferred embodiment, the agent is administered via a liposome carrier, e.g., a lecithin liposome or an alkylphospholipid liposome. The agent can be administered to the face, chest, neck, hands, and other regions of the body. The treatment can involve more than one administration, e.g., at least two, three, or four administrations, of the agent. The treatment can also involve daily administration of the agent.

In one embodiment, the method includes administering the agent in combination with a second treatment, e.g., a second treatment for skin, e.g., a sunscreen, antibiotic, moisturizer, a retinoic acid, a retinoid derivative, or an alpha-hydroxy acid. In some embodiments, the agent is administered to the subject in combination with a controlled release device, e.g., a biocompatible polymer, micro particle, or mesh. The device can reduce degradation and control the release of the agent.

In some embodiments, the method includes evaluating the subject for skin damage. The evaluation can be performed before, during, and/or after the administration of the agent. For example, the evaluation can be performed at least 4 hours, 8 hours, 12 hours, 1 day, 2 days, 4, 7, 14, or more days before and/or after the administration.

In a preferred embodiment, the administration of an agent can be performed: prior to exposure to UVB light, e.g., prior to sun exposure; when chronic or acute-UVB induced skin damage (e.g., sunburn, selling, redness, and/or inflammation) is noticed or diagnosed; at the time a treatment for a skin damage-related disorder is begun or begins to exert its effects; or generally, as is needed to maintain skin health.

The period over which the agent is administered, or the period over which clinically effective levels are maintained in the subject, can be short term, e.g., for one day, two days, one week, or long term, e.g., for six months or more or a year or more, or short term, e.g., for less than a year, six months, one month, two weeks or less.

The identification of a subject in need of altered skin damage can be performed e.g., by the subject, by a health care provider, by a provider of a skin damage treatment, or another party. The agent may be administered, e.g., by the subject, by a health care provider, by a provider of a skin damage treatment, or another party. Likewise, the evaluation of the effect on skin damage may be performed, e.g., by the subject, by a health care provider, by a provider of a skin damage treatment, or another party.

An agent that decreases VEGF-A signaling can be, for example: a VEGF-A binding protein or VEGFR-2 binding protein. For example, such binding proteins can bind and inhibit VEGF-A or bind and inhibit VEGFR-2 activity. The binding protein may inhibits the ability of VEGF-A or VEGFR-2 to interact with each other or another binding partner. In one embodiment, the binding protein is an antibody that specifically binds to VEGF-A or VEGFR-2, e.g., an antibody that disrupts VEGF's or VEGFR-2's ability to bind to a binding partner or to each other. Another exemplary agent is a mutated inactive VEGF-A that binds to VEGF-A or VEGFR-2 but disrupts VEGF signaling. Still another exemplary agent is VEGFR-2 (e.g., a non-signaling variant) or fragment thereof (e.g., an extracellular domain of VEGFR-2)

that binds to VEGF-A or VEGFR-2 but disrupts VEGF-A signaling. Additional exemplary agents include a VEGF-A or VEGFR-2 nucleic acid molecule that can bind to a cellular VEGF-A or VEGFR-2 nucleic acid sequence, e.g., mRNA, and can inhibit expression of the protein, e.g., an antisense, siRNA molecule or ribozyme; an agent that decreases VEGF-A or VEGFR-2 gene expression, e.g., a small molecule that binds the promoter of VEGF-A or VEGFR-2; or a crude or semi-purified extract, e.g., a botanical extract such as a plant extract, or algal extract.

For example, subjects can be treated with VEGF antagonists, e.g., anti-VEGF antibodies such as bevacizumab; or VEGF receptor antagonists, e.g., anti-VEGF receptor antibodies or small molecule inhibitors, compounds having a molecular weight of less than 1500 daltons.

Exemplary inhibitors and VEGF receptor antagonists include inhibitors of VEGF receptor tyrosine kinase activity. 4-[4-(1-Amino-1-methylethyl)phenyl]-2-[4-(2-morpholin-4-yl-ethyl)phenylamino]pyrimidine-5-carbonitrile (JNJ-17029259) is one of a structural class of 5-cyanopyrimidines that are orally available, selective, nanomolar inhibitors of the vascular endothelial growth factor receptor-2 (VEGF-R2). Additional examples include: PTK-787/ZK222584 (Astra-Zeneca), SU5416, SU11248 (Pfizer), and ZD6474 ([N-(4-bromo-2-fluorophenyl)-6-methoxy-7-[(1-methylpiperidin-4-yl)methoxy]quinazolin-4-amine]). Still other agents that can be used are broad specificity tyrosine kinase inhibitors, e.g., SU6668. See, e.g., Bergers, B. et al. (2003) J. Clin. Invest. 111, 1287-1295.

In another preferred embodiment, VEGF-A or VEGFR-2 is inhibited by decreasing the level of expression of an endogenous VEGF-A or VEGFR-2 gene, e.g., by decreasing transcription of the VEGF-A or VEGFR-2 gene. In a preferred embodiment, transcription of the VEGF-A or VEGFR-2 gene can be decreased by: altering the regulatory sequences of the endogenous VEGF-A or VEGFR-2 gene, e.g., by the addition of a negative regulatory sequence, such as a DNA-binding site for a transcriptional repressor, or by the removal of a positive regulatory sequence, such as an enhancer or a DNA-binding site for a transcriptional activator. In another preferred embodiment, the antibody that binds VEGF-A or VEGFR-2 is a monoclonal antibody, e.g., a humanized chimeric or human monoclonal antibody.

In one embodiment, an agent that decreases VEGF expression is a VEGF-A or VEGFR-2 nucleic acid molecule that can bind to a cellular VEGF-A or VEGFR-2 nucleic acid sequence, e.g., mRNA, and can inhibit expression of the protein, e.g., an antisense, siRNA molecule or ribozyme; an agent that decreases VEGF-A or VEGFR-2 gene expression, e.g., a small molecule that binds the promoter of VEGF-A or VEGFR-2; or a crude or semi-purified extract, e.g., a botanical extract such as a plant extract, or algal extract, e.g., pomegranate seed oil or grape seed oil.

The method can further include: increasing the activity of one or more lymphogenic factors, e.g., increasing the activity of naturally occurring lymphogenic proteins such as VEGF-C or -D or VEGFR (e.g., VEGFR-3) in the subject. VEGF-C or -D or VEGFR (e.g., VEGFR-3) activity can be increased, e.g., by administering an agent which increases a VEGF-C or -D or VEGFR (e.g., VEGFR-3) activity. In a preferred embodiment, an agent which increases a VEGF-C or -D or VEGFR (e.g., VEGFR-3) activity can be one or more of the following: a VEGF-C or -D polypeptide, or a biologically active fragment or analog thereof, e.g., a VEGF-C or -D derived polypeptide or retro-inverso polypeptide thereof; a nucleic acid encoding a VEGF-C or -D polypeptide, or a biologically active fragment or analog thereof; an agonist of VEGF-C or -D, e.g., an antibody or a small molecule having or increasing VEGF-C or -D activity; or an agent that increases VEGF-C or -D nucleic acid expression, e.g., a small molecule which binds to the promoter region of VEGF-C or -D and increases expression.

In a preferred embodiment, VEGF-C or -D or VEGFR (e.g., VEGFR-3) is increased by an agent, e.g., a small molecule, which induces VEGF-C or -D or VEGFR (e.g., VEGFR-3) expression. In preferred embodiments, an agent that induces VEGF-C or -D or VEGFR (e.g., VEGFR-3) expression is administered topically. In preferred embodiments, the agent is administered to a subject sufficiently before UVB exposure, e.g., sun exposure, such that a lymphogenesis effect is present in the subject's skin at the time of UVB exposure.

VEGF-C or -D or VEGFR (e.g., VEGFR-3) activity can also be increased by controlled delivery to the subject of a VEGF-C or -D or VEGFR (e.g., VEGFR-3) nucleic acid, or a VEGF-C or -D or VEGFR (e.g., VEGFR-3) protein, fragment, or analog. A VEGF-C or -D or VEGFR (e.g., VEGFR-3) nucleic acid, protein, fragment, or analog can be administered to the subject in combination with a controlled release device, e.g., a biocompatible polymer, micro particle, or mesh. The device can reduce degradation and control the release of the VEGF-C or -D or VEGFR (e.g., VEGFR-3) nucleic acid, protein, fragment, or analog. Such a VEGF-C or -D or VEGFR (e.g., VEGFR-3) biocompatible controlled release system can be administered to the subject, e.g., by injection or implantation, e.g., intramuscularly, subcutaneously, intravenously, or at an organ, joint cavity, or at a lesion.

The level of VEGF-C or -D or VEGFR (e.g., VEGFR-3) can also be increased by increasing the endogenous VEGF-C or -D or VEGFR (e.g., VEGFR-3) activity. Activity can be increased by increasing the level of expression of the gene, e.g., by increasing transcription of the VEGF-C or -D or VEGFR (e.g., VEGFR-3) gene; increasing the stability of the VEGF-C or -D or VEGFR (e.g., VEGFR-3) mRNA, e.g., by altering the secondary or tertiary structure of the mRNA; increasing the translation of VEGF-C or -D or VEGFR (e.g., VEGFR-3) mRNA, e.g., by altering the sequence of the VEGF-C or -D or VEGFR (e.g., VEGFR-3) mRNA; and/or increasing the stability of the VEGF-C or -D or VEGFR (e.g., VEGFR-3) protein. Transcription of the VEGF-C or -D or VEGFR (e.g., VEGFR-3) gene can be increased, e.g., by altering the regulatory sequences of the endogenous VEGF-C or -D or VEGFR (e.g., VEGFR-3) gene. In one embodiment the regulatory sequence can be altered by: the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the VEGF-C or -D or VEGFR (e.g., VEGFR-3) gene to be transcribed more efficiently.

In one embodiment, the agent is a composition, e.g., small molecule or a crude or semi-purified extract, e.g., a botanical extract such as a plant extract, that induces VEGF-C or -D or VEGFR (e.g., VEGFR-3).

In another aspect, the invention features compositions containing an agent, e.g., an agent described herein, e.g., an agent identified by a screening method described herein, that decreases the expression, activity, or level of VEGF-A or VEGFR (e.g., VEGFR-2), for reducing chronic or acute UVB-induced skin damage. In a preferred embodiment, the composition is a cosmetic composition, e.g., formulated for topical administration. In a preferred embodiment, the composition also has a fragrance, a preservative, or other cosmetic ingredient, e.g., a moisturizer, or sunscreen agent, e.g., octyl methoxycinnamate, aminobenzoic acid, oxybenzone, padimate O, homosalate, or titanium dioxide. The composition can be provided in a shampoo, oil, cream, lotion, soap, foam, gel, or other cosmetic preparation. In a preferred embodiment, the composition also has a cosmetic ingredient, e.g., a fragrance or moisturizer.

In another aspect, the invention features the use of an agent, e.g., an agent described herein, e.g., an agent identified by a screening method described herein, that decreases the expression, activity, or level of VEGF-A or VEGFR (e.g., VEGFR-2), for the preparation of a medicament for reducing chronic or acute UVB-induced skin damage. In some embodiments, the medicament further comprises an agent that increases the expression, activity, or level of VEGF-C, VEGF-D or VEGFR-3.

In another aspect, the invention features a method of modulating skin damage in a subject. The method includes supplying to the subject a composition containing an agent that affects the expression, activity or level of a component of VEGF-A or VEGFR (e.g., VEGFR-2), e.g., an agent described herein, e.g., an agent identified by a screening method described herein, and supplying to the subject instructions for application of the agent, e.g., to treat skin damage such as acute UVB-induced skin damage.

In another aspect, the invention features a kit for modulating skin damage of a subject that includes a composition described herein, e.g., a composition containing an agent that affects the expression, activity, or level of a component of VEGF or VEGFR (e.g., VEGFR-2); and instructions for use, e.g., instructions to apply the composition to an area of the body in need of treatment for acute UVB-induced skin damage, e.g., redness, swelling, sunburn and/or inflammation. In a preferred embodiment, the composition also has a cosmetic ingredient, e.g., a fragrance or moisturizer.

An effective amount of the agent of the present invention is defined as the amount of a composition that, upon administration to a subject (e.g., a human), reduces skin damage in the subject. The effective amount to be administered to a subject is typically based on a variety of factors including age, sex, surface area, weight, and conditions of the skin. Body surface area may be approximately determined from height and weight of the patient. See, e.g., Scientific Tables, Geigy Pharmaceuticals, Ardley, N.Y., 1970, 537. Effective doses will vary, as recognized by those skilled in the art, dependent on route of administration, excipient usage, and the possibility of co-usage with other treatments such as usage of other skin damage-modulating compounds.

In another aspect, the invention features a method that includes: applying, to a skin region of a human subject, (e.g., forearms, legs, back, torso, head, face, scalp, a protective amount of a VEGF signaling inhibitor; and exposing the subject to irradiation, e.g., to sunlight, e.g., direct or high intensity sunlight, or to a UV-light, e.g., as in a tanning parlor. A protective amount is an amount sufficient to reduced skin damage to a detectable or statistically significant level In another aspect, the invention features methods of monitoring a subject or cells from a subject, e.g., skin cells. The methods include evaluating expression of one or more of VEGF-A, -C, and -D. An increase in VEGF-A levels and a decrease in VEGF-C or -D levels, relative to a reference (e.g., control or un-irradiated cells) can indicate that the subject or cells from the subject are at risk for or have been exposed to a skin damaging condition, e.g., irradiation, e.g., UVB irradiation.

As used herein, exposure to UVB-radiation means exposure to natural sunlight or artificial UVB radiation (e.g., a UVB sun lamp, e.g., for tanning, or for phototherapy, e.g., for treatment of psoriasis, atopic dermatitis, or vitiligo) of at least one MED.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1E depicts the area covered by lymphatic vessels in skin samples from chronic UVB-irradiated and sham irradiated mice. FIG. 1F depicts the average size of lymphatic vessels in skin samples from chronic UVB-irradiated and sham irradiated mice. FIG. 1G depicts the density of lymphatic vessels in skin samples from chronic UVB-irradiated and sham irradiated mice. The area covered by lymphatic vessels (FIG. 1E) and the average size of the lymphatic vessels (FIG. 1F) were significantly increased in UVB-irradiated skin as compared to sham-irradiated skin (**, p<0.01).

FIGS. 2A-C depict sham-irradiated mice. FIGS. 2D-F depict chronically UVB-irradiated mice. Dye spreading is shown at 1 minute (FIGS. 2A and 2D), 3 minutes (FIGS. 2B and 2E), and 5 minutes (FIGS. 2C and 2F) after injection. At 1 and 3 minutes after ink injection, markedly dilated lymphatic vessels were visualized in chronically UVB-irradiated mouse skin (FIGS. 2D-E), as compared with sham-irradiated mice (FIGS. 2A-B). After 5 minutes, Evans blue dye had extravasated from lymphatic vessels in chronically UVB-irradiated skin (FIG. 2F), whereas no such leakage was observed in sham-irradiated mice (FIG. 2C).

FIGS. 4A-C depict sham-irradiated mice (0 mJ/cm$^2$). FIGS. 4D-F depict mice two days after a single dose of 40 mJ/cm$^2$ UVB (0.5 MED). FIGS. 4G-I depict mice two days after a single dose of 80 mJ/cm$^2$ UVB (1 MED). Dye spreading is shown at 1 minute (FIGS. 2A, 2D, and 2G), 3 minutes (FIGS. 2B, 2E, and 2H), and 5 minutes (FIGS. 2C, 2F, and 2I) after injection. Irradiation with a dose of 80 mJ/cm$^2$ of UVB (1 MED) resulted in enlargement of cutaneous lymphatic vessels (FIGS. 4G-H), and pronounced leakiness (FIG. 4I).

FIG. 5E depicts the average size of lymphatic vessels in skin samples from chronic UVB-irradiated and sham irradiated wild-type and VEGF transgenic mice. FIG. 5F depicts the density of lymphatic vessels in skin samples from chronic UVB-irradiated and sham irradiated wild-type and VEGF transgenic mice. Morphometric analyses showed a 1,3-fold increase of lymphatic vessel size in sham-irradiated VEGF transgenic mice compared to wild type mice (*, p<0.05), and a 1,9-fold enlargement after UVB irradiation (**, p<0.01)(FIG. 5E). The density of lymphatic vessels was comparable in all groups (FIG. 5F).

DETAILED DESCRIPTION

Figure 1:
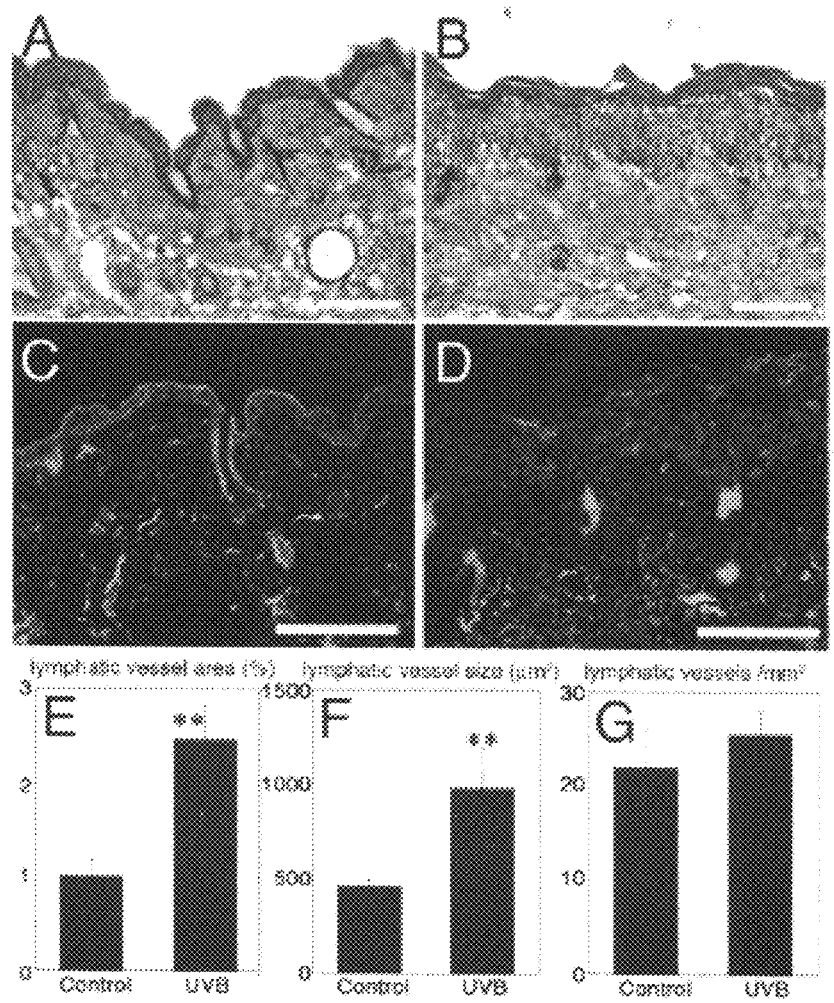
FIGS. 1A-B are a micrograph of hematoxylin/eosin-stained skin tissue samples showing enlargement of lymphatic vessels after chronic UVB irradiation (FIG. 1B), but not in sham-irradiated skin (FIG. 1A). Scale bars: 100 µm.
FIG. 1C-D are immunofluorescence micrographs for CD31 and LYVE-1 in UVB-irradiated (FIG. 1D) and sham-irradiated (FIG. 1C) skin tissue samples. UVB-irradiated skin samples showed moderate enlargement of CD31+/LYVE-1– blood vessels in UVB-irradiated skin (FIG. 1D). LYVE-1-positive cutaneous lymphatic vessels were greatly increased in size, with irregular shapes and sometimes incomplete endothelial cell lining, whereas only normal, collapsed lymphatic vessels were found in sham-irradiated mice (FIG. 1D). Scale bars: 100 µm.
FIGS. 1E-G are bar graphs depicting morphometric analyses of skin samples from chronic UVB-irradiated and sham irradiated mice.

Ultraviolet B (UVB) irradiation of the skin induces erythema, degradation of extracellular matrix molecules, and skin wrinkling. Lymphatic vessels play an important role in maintaining the fluid balance in normal skin. We found that both acute and chronic UVB-irradiation of murine skin results in prominent enlargement of lymphatic vessels. Surprisingly, these enlarged lymphatic vessels were functionally impaired and were hyperpermeable, as detected by intravital lymphangiography. The expression levels of vascular endothelial growth factor (VEGF)-A, but not of VEGF-C or -D were enhanced in UVB-irradiated epidermis. Targeted overexpression of VEGF-A in the epidermis of transgenic mice led to increased enlargement and, surprisingly, also to leakage of lymphatic vessels after acute UVB irradiation, whereas systemic blockade of VEGF-A signaling largely prevented lymphatic vessel abnormalities and also prevented photodamage induced by UVB. Together, these findings indicate lymphatic vessels as novel targets for preventing UVB-induced cutaneous photodamage, and they also suggest that promotion of lymphatic function, for example by lymphangiogenic factors such as VEGF-C, may ameliorate the damaging effects of UVB irradiation—that are mediated in part by VEGF-A—on the skin. Accordingly, this application features methods of treating (e.g., reducing, ameliorating, or preventing) skin damage (e.g., induced by UVB) by decreasing the levels or activity of VEGF-A or VEGFR (e.g., VEGFR-2), e.g., in the skin, of a subject.

VEGF and VEGF receptors are reviewed, e.g., in Shibuya and Claesson-Welsh (2006) Exp. Cell Res. 312:549-60; Byrne et al. (2005) J. Cell. Mol. Med. 9:777-94; and Coultas et al. (2005) Nature 438:937-45.

UVB Damage

The UV index (developed by the United States Environmental Protection Agency) indicates the intensity of the sun's UV rays on a given day. There are four categories—moderate (UV index is less than 3), high (UV index is 3 to 6) very high (UV index is 6 to 10) and extreme (UV index is greater than 10). A moderate UV Index means it will take more than an hour to burn your skin; an extreme level means it will take less than 15 minutes. The index is often included with weather reports. Clinically, UVB exposure is measured in minimal erythema doses (MED). One MED is the amount of UVB required to produce a sunburn in sensitive skin. Moderate-to-severe acute UVB-induced skin damage, e.g., sunburn, can occur at 3-8 MEDs.

Screening Methods

Numerous methods exist for evaluating whether an agent can modulate VEGF-A signaling, e.g., VEGF-A or VEGFR gene expression, activity or level. In one embodiment, the ability of a test agent to modulate, e.g., increase or decrease, e.g., permanently or temporarily, expression from a VEGF-A or VEGFR (e.g., VEGFR-2) gene promoter is evaluated by e.g., routine reporter (e.g., LacZ or GFP or luciferase) transcription assay. For example, a cell or transgenic animal whose genome comprises a reporter gene operably linked to a VEGF-A or VEGFR (e.g., VEGFR-2) promoter, can be contacted with a test agent, and the ability of the test agent to increase or decrease reporter activity is indicative of the ability of the agent to modulate acute UVB skin damage. In another embodiment, the ability of a test agent to modulate VEGF-A or VEGFR (e.g., VEGFR-2) gene expression, or VEGF-A or VEGFR (e.g., VEGFR-2) activity or level, is evaluated in a transgenic animal, for example, the transgenic animal described herein.

The effect of a test agent on VEGF-A or VEGFR (e.g., VEGFR-2) gene expression or VEGF-A or VEGFR (e.g., VEGFR-2) activity or level may also be evaluated in a cell, cell lysate, or subject, preferably a non-human experimental mammal, and more preferably a rodent (e.g., a rat, mouse, or rabbit), or explant (e.g., skin) thereof. Methods of assessing VEGF-A or VEGFR (e.g., VEGFR-2) gene expression are well know in the art, e.g., Northern analysis, ribonuclease protection assay, reverse transcription-polymerase chain reaction (RT-PCR) or RNA in situ hybridization (see, e.g., Sambrook et al. *Molecular Cloning: A Laboratory Manual* (3$^{rd}$ ed. 2001)). The level of VEGF-A or VEGFR (e.g., VEGFR-2) may be monitored by, e.g., Western analysis, immunoassay, or in situ hybridization. VEGF-A or VEGFR (e.g., VEGFR-2) activity, e.g., altered promoter binding and/or transcription activity, may be determined by, e.g., electrophoretic mobility shift assay, DNA footprinting or reporter gene assay. Preferably, the effect of a test agent on VEGF-A or VEGFR (e.g., VEGFR-2) gene expression or VEGF-A or VEGFR (e.g., VEGFR-2) activity or level is observed as a change in skin damage in a subject. More preferably, the effect of a test agent on VEGF-A or VEGFR (e.g., VEGFR-2) gene expression or VEGF-A or VEGFR (e.g., VEGFR-2) activity or level is evaluated on a transgenic cell or non-human animal, or explant or cell derived therefrom, having altered VEGF signaling, as compared to a wild-type cell or non-human animal, or explant or cell derived therefrom.

The test agent may be administered to a cell, cell extract, explant or subject expressing a transgene comprising the VEGF-A or VEGFR (e.g., VEGFR-2) gene promoter fused to LacZ. (Enhancement or inhibition of transgene, e.g., a reporter, e.g., LacZ or GFP, transcription, as a result of an effect of the test agent on the VEGF-A or VEGFR (e.g., VEGFR-2) gene promoter or factors regulating transcription from the VEGF-A or VEGFR (e.g., VEGFR-2) gene promoter, may be easily observed as a change in color. Reporter transcript levels, and thus VEGF-A or VEGFR (e.g., VEGFR-2) gene promoter activity, may be monitored by established methods, e.g., Northern analysis, ribonuclease protection assay, reverse transcription-polymerase chain reaction (RT-PCR) or RNA in situ hybridization (see, e.g., Cuncliffe et al. (2002) Mamm. Genome 13:245). Agents may be evaluated using a cell-free system, e.g., an environment comprising the VEGF-A or VEGFR (e.g., VEGFR-2) gene promoter-reporter transgene (e.g., VEGF-A or VEGFR (e.g., VEGFR-2) gene promoter-LacZ transgene), transcription factors binding the VEGF-A or VEGFR (e.g., VEGFR-2) gene promoter, a crude cell lysate or nuclear extract, and the test agent (e.g., an agent described herein), wherein an effect of the agent on VEGF-A or VEGFR (e.g., VEGFR-2) gene promoter activity is detected as a color change.

In some embodiments, VEGF-A, and biologically active fragments thereof are provided as purified polypeptides. Purified polypeptides include polypeptides that are generated in vitro (e.g., by in vitro translation or by use of an automated polypeptide synthesizer) and polypeptides that are initially expressed in a cell (e.g., a prokaryotic cell, a eukaryotic cell, an insect cell, a yeast cell, a mammalian cell, a plant cell) and subsequently purified. Cells that express a purified polypeptide can include cells that encode an endogenous gene, cells transduced with an expression vector encoding a polypeptide, and cells that are experimentally manipulated to induce expression of an endogenous gene that is not typically expressed in that cell type (e.g., gene activation technology). In some embodiments, polypeptides are fusion proteins (e.g., an VEGFR-glutathione-5-transferase fusion) that may include a protease cleavage site to allow cleavage and separation of the fusion protein into separate polypeptides. In some embodiments, a polypeptide can include an amino acid sequence that facilitates purification of the polypeptide (e.g., a multiple histidine tag, a FLAG tag, etc). Methods for isolating proteins from cells or polypeptides that are expressed by cells, include affinity purification, size exclusion chromatography, high performance liquid chromatography, and other chromatographic purification methods. The polypeptides can be post-translationally modified, e.g., glycosylated.

In another aspect, the invention includes methods for screening test compounds to identify a compound that modulates a protein-protein interaction between a VEGF-A polypeptide and a VEGFR (e.g., VEGFR-2) polypeptide. A method useful for high throughput screening of compounds capable of modulating protein-protein interactions between transcriptional regulators is described in Lepourcelet et al., Cancer Cell 5: 91-102 (2004), which is incorporated herein by reference in its entirety. Typically, a first compound is provided. The first compound is a VEGF-A polypeptide or biologically active fragment thereof, or the first compound is a VEGFR (e.g., VEGFR-2) polypeptide, or biologically active fragment thereof. A second compound is provided which is different from the first compound, and which is labeled. The second compound is an VEGF-A polypeptide or biologically active fragment thereof, or the second compound VEGFR (e.g., VEGFR-2) polypeptide, or biologically active fragment thereof. A test compound is provided. The first compound, second compound, and test compound are contacted with each other. The amount of label bound to the first compound is then determined. A change in protein-protein interaction between the first compound and the second compound as assessed by label bound is indicative of the usefulness of the compound in modulating a protein-protein interaction between the VEGF-A and the VEGFR (e.g., VEGFR-2) polypeptide. In some embodiments, the change is assessed relative to the same reaction without addition of the test compound.

In certain embodiments, the first compound provided is attached to a solid support. Solid supports include, e.g., resins, e.g., agarose, beads, and multiwell plates. In certain embodiments, the method includes a washing step after the contacting step, so as to separate bound and unbound label.

In certain embodiments, a plurality of test compounds is contacted with the first compound and second compound. The different test compounds can be contacted with the other compounds in groups or separately. In certain embodiments, each of the test compounds is contacted with both the first compound and the second compound in separate wells. For example, the method can screen libraries of test compounds. Libraries of test compounds are discussed in detail above. Libraries can include, e.g., natural products, organic chemicals, peptides, and/or modified peptides, including, e.g., D-amino acids, unconventional amino acids, and N-substituted amino acids. Typically, the libraries are in a form compatible with screening in multiwell plates, e.g., 96-well plates. The assay is particularly useful for automated execution in a multiwell format in which many of the steps are controlled by computer and carried out by robotic equipment. The libraries can also be used in other formats, e.g., synthetic chemical libraries affixed to a solid support and available for release into microdroplets.

In certain embodiments, the first compound is an VEGF-A polypeptide, or fragment thereof, and the second compound is a VEGFR (e.g., VEGFR-2) polypeptide, or a fragment thereof. The solid support to which the first compound is attached can be, e.g., sepharose beads, SPA beads (microspheres that incorporate a scintillant) or a multiwell plate. SPA beads can be used when the assay is performed without a washing step, e.g., in a scintillation proximity assay. Sepharose beads can be used when the assay is performed with a washing step. The second compound can be labeled with any label that will allow its detection, e.g., a radiolabel, a fluorescent agent, biotin, a peptide tag, or an enzyme fragment. The second compound can also be radiolabeled, e.g., with $^{125}$I or $^{3}$H.

In certain embodiments, the enzymatic activity of an enzyme chemically conjugated to, or expressed as a fusion protein with, the first or second compound, is used to detect bound protein. A binding assay in which a standard immunological method is used to detect bound protein is also included. In certain other embodiments, the interaction of a VEGF-A polypeptide, or fragment thereof, and a VEGFR (e.g., VEGFR-2) polypeptide, or fragment thereof, is detected by fluorescence resonance energy transfer (FRET) between a donor fluorophore covalently linked to VEGF-A (e.g., a fluorescent group chemically conjugated to VEGF-A, or a variant of green fluorescent protein (GFP) expressed as an VEGF-A-GFP chimeric protein) and an acceptor fluorophore covalently linked to a VEGFR (e.g., VEGFR-2) polypeptide, or fragment thereof, where there is suitable overlap of the donor emission spectrum and the acceptor excitation spectrum to give efficient nonradiative energy transfer when the fluorophores are brought into close proximity through the protein-protein interaction of a VEGF-A polypeptide and a VEGFR (e.g., VEGFR-2) polypeptide.

In other embodiments, the protein-protein interaction is detected by reconstituting domains of an enzyme, e.g., β-galactosidase (see Rossi et al., Proc. Natl. Acad. Sci. USA 94:8405-8410 (1997)).

In still other embodiments, the protein-protein interaction is assessed by fluorescence ratio imaging (Bacskai et al., Science 260:222-226 (1993)) of suitable chimeric constructs of $EspF_U$ polypeptides and Tir or N-WASP polypeptides in cells, or by variants of the two-hybrid assay (Fearon et al., Proc. Natl. Acad. Sci. USA 89:7958-7962 (1992); Takacs et al., Proc. Natl. Acad. Sci. USA 90:10375-10379 (1993); Vidal et al., Proc. Natl. Acad. Sci. USA 93:10315-10320 (1996); Vidal et al., Proc. Natl. Acad. Sci. USA 93:10321-10326 (1996)) employing suitable constructs of VEGF-A and VEGFR (e.g., VEGFR-2) polypeptides and tailored for a high throughput assay to detect compounds that inhibit the VEGF-A/VEGFR interaction. These embodiments have the advantage that the cell permeability of compounds that act as modulators in the assay is assured.

For example, in one assay, but not the only assay, VEGF-A polypeptides or fragment thereof, are adsorbed to ELISA plates. VEGF-A polypeptides are then exposed to test compounds, followed by glutathione-5-transferase (GST)-VEGFR (e.g., VEGFR-2) polypeptide fusion proteins. Bound protein is detected with goat anti-GST antibody, alkaline phosphatase (AP)-coupled anti-goat IgG, and AP substrate. Compounds that interfere with protein-protein interactions yield reduced AP signals in the ELISA plates.

Exemplary Agents

A variety of agents can be used as a VEGF (e.g., VEGF-A, -C, or -D) or VEGFR (e.g., VEGFR-2 or -3) modulator to treat or prevent skin damage. The agent may be any type of compound that can be administered to a subject (e.g., antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, natural products and extracts, and the like). In one embodiment, the VEGF/VEGFR modulator is a biologic, e.g., a protein having a molecular weight of between 5-300 kDa.

For example, a VEGF/VEGFR modulator may inhibit binding of VEGF to a VEGFR or may prevent VEGF-mediated signal transduction, e.g., as transduced by the VEGFR protein, e.g., VEGFR-2. A VEGF/VEGFR modulator that binds to VEGF may alter the conformation of VEGF, hinder binding of VEGF to VEGFR, or otherwise decrease the affinity of VEGF for a VEGFR or prevent the interaction between VEGF and a VEGFR. Alternately, a VEGF/VEGFR modulator may stimulate binding of VEGF to a VEGFR or may induce VEGFR signal transduction by activating the VEGFR in the absence of a VEGF.

A VEGF/VEGFR modulator (e.g., an antibody) may bind to VEGF or to a VEGFR with a $K_d$ of less than $10^{-6}$, $10^{-7}$, $10^{-8}$, $10^{-9}$, or $10^{-10}$ M. In one embodiment, the VEGF/VEGFR modulator binds to VEGF (i.e., VEGF-A with an affinity at least 5, 10, 20, 50, 100, 200, 500, or 1000 better than its affinity for a non-VEGF-A protein, e.g., VEGF-C or VEGF-D). A preferred VEGF/VEGFR modulator specifically binds to VEGF or VEGFR, such as a VEGF or VEGFR specific antibody.

Exemplary VEGF/VEGFR modulators include antibodies that bind to VEGF or VEGFR and soluble forms of the VEGFR that compete with cell surface VEGFR for binding to VEGF. An example of a soluble form of VEGFR is a protein that includes at least a portion of the extracellular domain of a VEGFR (e.g., a soluble VEGF-binding fragment of VEGFR-2 or VEGFR-3, e.g., including a portion that binds to VEGF).

An exemplary soluble form of the VEGFR protein includes a region of the VEGFR protein that binds to VEGF, e.g., an extracellular domain, e.g., domain of in the extracellular region. This region can be physically associated, e.g., fused to another amino acid sequence, e.g., an Fc domain, at its N- or C-terminus. The region from VEGFR can be spaced by a linker from the heterologous amino acid sequence. Other soluble forms of VEGFR, e.g., forms that do not include an Fc domain, can also be used.

Exemplary VEGF/VEGFR modulators include antibodies that bind to VEGF and/or VEGFR. In one embodiment, the antibody inhibits the interaction between VEGF and a VEGFR, e.g., by physically blocking the interaction, decreasing the affinity of VEGF and/or VEGFR for its counterpart, disrupting or destabilizing VEGF complexes, sequestering VEGF or a VEGFR, or targeting VEGF or VEGFR for degradation. In one embodiment, the antibody can bind to VEGF or VEGFR at an epitope that includes one or more amino acid residues that participate in the VEGF/VEGFR binding interface. Such amino acid residues can be identified, e.g., by alanine scanning. In another embodiment, the antibody can bind to residues that do not participate in the VEGF/VEGFR binding. For example, the antibody can alter a conformation of VEGF or VEGFR and thereby reduce binding affinity, or the antibody may sterically hinder VEGF/VEGFR binding.

In addition to antibodies that bind to VEGF and/or VEGFR, other antibodies can be used. In one embodiment, the antibody can prevent activation of a VEGF/VEGFR mediated event or activity.

As used herein, the term "antibody" refers to a protein that includes at least one immunoglobulin variable region, e.g., an amino acid sequence that provides an immunoglobulin variable domain or an immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')₂ fragments, Fd fragments, Fv fragments, and dAb fragments) as well as complete antibodies, e.g., intact and/or full length immunoglobulins of types IgA, IgG (e.g., IgG1, IgG2, IgG3, IgG4), IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity, or may be non-functional for one or both of these activities.

The VH and VL regions can be further subdivided into regions of hypervariability, termed "complementarity determining regions" ("CDR"), interspersed with regions that are more conserved, termed "framework regions" (FR). The extent of the FR's and CDR's has been precisely defined (see, Kabat, E. A., et al. (1991) *Sequences of Proteins of Immuno-* logical Interest, Fifth Edition, US Department of Health and Human Services, NIH Publication No. 91-3242; and Chothia, C. et al. (1987) *J. Mol. Biol.* 196:901-917). Kabat definitions are used herein. Each VH and VL is typically composed of three CDR's and four FR's, arranged from amino-terminus to carboxyl-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two β-sheets formed of about seven β-strands, and a conserved disulfide bond (see, e.g., A. F. Williams and A. N. Barclay (1988) *Ann. Rev Immunol.* 6:381-405). An "immunoglobulin variable domain sequence" refers to an amino acid sequence that can form a structure sufficient to position CDR sequences in a conformation suitable for antigen binding. For example, the sequence may include all or part of the amino acid sequence of a naturally-occurring variable domain. For example, the sequence may omit one, two, or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with VEGFR.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2, and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

One or more regions of an antibody can be human, effectively human, or humanized. For example, one or more of the variable regions can be human or effectively human. For example, one or more of the CDRs, e.g., HC CDR1, HC CDR2, HC CDR3, LC CDR1, LC CDR2, and LC CDR3, can be human. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical, or completely identical, to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762. In some cases, humanized immunoglobulins can include a non-human amino acid at one or more framework amino acid positions.

Antibodies that bind to VEGF or a VEGFR can be generated by a variety of means, including immunization, e.g., using an animal, or in vitro methods such as phage display. All or part of VEGF or VEGFR can be used as an immunogen or as a target for selection. For example, VEGF or a fragment thereof, VEGFR or a fragment thereof, can be used as an immunogen. In one embodiment, the immunized animal contains immunoglobulin producing cells with natural, human, or partially human immunoglobulin loci. In one embodiment, the non-human animal includes at least a part of a human immunoglobulin gene. For example, it is possible to engineer mouse strains deficient in mouse antibody production with large fragments of the human Ig loci. Accordingly, by using hybridoma technology, at least partly human, antigen-specific monoclonal antibodies with the desired specificity can be produced and selected. See, e.g., XENOMOUSE™, Green et al. (1994) *Nat. Gen.* 7:13-21; US 2003-0070185; U.S. Pat. No. 5,789,650; and WO 96/34096.

Non-human antibodies to VEGF and VEGFR can also be produced, e.g., in a rodent. The non-human antibody can be humanized, e.g., as described in EP 239 400; U.S. Pat. Nos. 6,602,503; 5,693,761; and 6,407,213, deimmunized, or otherwise modified to make it effectively human.

EP 239 400 (Winter et al.) describes altering antibodies by substitution (within a given variable region) of their complementarity determining regions (CDRs) for one species with those from another. Typically, CDRs of a non-human (e.g., murine) antibody are substituted into the corresponding regions in a human antibody by using recombinant nucleic acid technology to produce sequences encoding the desired substituted antibody. Human constant region gene segments of the desired isotype (usually gamma I for CH and kappa for CL) can be added and the humanized heavy and light chain genes can be co-expressed in mammalian cells to produce soluble humanized antibody. Other methods for humanizing antibodies can also be used. For example, other methods can account for the three dimensional structure of the antibody, framework positions that are in three dimensional proximity to binding determinants, and immunogenic peptide sequences. See, e.g., WO 90/07861; U.S. Pat. Nos. 5,693, 762; 5,693,761; 5,585,089; and 5,530,101; Tempest et al. (1991) *Biotechnology* 9:266-271 and U.S. Pat. No. 6,407, 213.

Fully human monoclonal antibodies that bind to VEGF and VEGFR can be produced, e.g., using in vitro-primed human splenocytes, as described by Boerner et al. (1991) *J. Immunol.* 147:86-95. They may be prepared by repertoire cloning as described by Persson et al. (1991) *Proc. Nat. Acad. Sci. USA* 88:2432-2436 or by Huang and Stollar (1991) *J. Immunol. Methods* 141:227-236; also U.S. Pat. No. 5,798,230. Large non-immunized human phage display libraries may also be used to isolate high affinity antibodies that can be developed as human therapeutics using standard phage technology (see, e.g., Hoogenboom et al. (1998) *Immunotechnology* 4:1-20; Hoogenboom et al. (2000) *Immunol Today* 2:371-378; and US 2003-0232333).

Antibodies and other proteins described herein can be produced in prokaryotic and eukaryotic cells. In one embodiment, the antibodies (e.g., scFv's) are expressed in a yeast cell such as *Pichia* (see, e.g., Powers et al. (2001) *J. Immunol. Methods* 251:123-35), *Hanseula*, or *Saccharomyces*.

Antibodies, particularly full length antibodies, e.g., IgGs, can be produced in mammalian cells. Exemplary mammalian host cells for recombinant expression include Chinese Hamster Ovary (CHO cells) (including dihydrofolate reductase-negative CHO cells, described in Urlaub and Chasin (1980) *Proc. Natl. Acad. Sci. USA* 77:4216-4220, used with a DHFR selectable marker, e.g., as described in Kaufman and Sharp (1982) Mol. Biol. 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216; 4,634,665; and 5,179,017). Exemplary selectable marker genes include the dihydrofolate reductase (DHFR) gene (for use in dhfr⁻ host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr– CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G.

Antibodies (and Fc fusions) may also include modifications, e.g., modifications that alter Fc function, e.g., to decrease or remove interaction with an Fc receptor or with C1q, or both. For example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some proteins that include an Fc domain, the antibody/protein production system may be designed to synthesize antibodies or other proteins in which the Fc region is glycosylated. For example, the Fc domain of IgG molecules is glycosylated at asparagine 297 in the CH2 domain. The Fc domain can also include other eukaryotic post-translational modifications. In other cases, the protein is produced in a form that is not glycosylated.

Antibodies and other proteins can also be produced by a transgenic animal. For example, U.S. Pat. No. 5,849,992 describes a method for expressing an antibody in the mammary gland of a transgenic mammal. A transgene is constructed that includes a milk-specific promoter and nucleic acid sequences encoding the antibody of interest, e.g., an antibody described herein, and a signal sequence for secretion. The milk produced by females of such transgenic mammals includes, secreted-therein, the protein of interest, e.g., an antibody or Fc fusion protein. The protein can be purified from the milk, or for some applications, used directly.

Methods described in the context of antibodies can be adapted to other proteins, e.g., Fc fusions and soluble receptor fragments.

In certain implementations, nucleic acid antagonists are used to decrease expression of an endogenous gene encoding VEGF or a VEGFR. In one embodiment, the nucleic acid antagonist is an siRNA that targets mRNA encoding VEGF or a VEGFR. Other types of antagonistic nucleic acids can also be used, e.g., a dsRNA, a ribozyme, a triple-helix former, or an antisense nucleic acid. In some embodiments, nucleic acid antagonists can be directed to downstream effector targets of VEGFR activation.

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). siRNAs also include short hairpin RNAs (shRNAs) with 29-base-pair stems and 2-nucleotide 3' overhangs. See, e.g., Clemens et al. (2000) *Proc. Natl. Acad. Sci. USA* 97:6499-6503; Billy et al. (2001) *Proc. Natl. Sci. USA* 98:14428-14433; Elbashir et al. (2001) *Nature.* 411:494-8; Yang et al. (2002) *Proc. Natl. Acad. Sci. USA* 99:9942-9947; Siolas et al. (2005), *Nat. Biotechnol.* 23(2):227-31; 20040086884; U.S. 20030166282; 20030143204; 20040038278; and 20030224432.

Anti-sense agents can include, for example, from about 8 to about 80 nucleobases (i.e., from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA (e.g., an mRNA encoding VEGF or VEGFR) can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding VEGF or VEGFR. The complementary region can extend for between about 8 to about 80 nucleobases. The compounds can include one or more modified nucleobases. Modified nucleobases may include, e.g., 5-substituted pyrimidines such as 5-iodouracil, 5-iodocytosine, and C5-propynyl pyrimidines such as C5-propynylcytosine and C5-propynyluracil. Other suitable modified nucleobases include $N^4$—($C_1$-$C_{12}$) alkylaminocytosines and $N^4,N^4$—($C_1$-$C_{12}$) dialkylaminocytosines. Modified nucleobases may also include 7-substituted-8-aza-7-deazapurines and 7-substituted-7-deazapurines such as, for example, 7-iodo-7-deazapurines, 7-cyano-7-deazapurines, 7-aminocarbonyl-7-deazapurines. Examples of these include 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, and 2-amino-6-hydroxy-7-aminocarbonyl-7-deazapurines. Furthermore, $N^6$—($C_1$-$C_{12}$) alkylaminopurines and $N^6,N^6$—($C_1$-$C_{12}$) dialkylaminopurines, including $N^6$-methylaminoadenine and $N^6,N^6$-dimethylaminoadenine, are also suitable modified nucleobases. Similarly, other 6-substituted purines including, for example, 6-thioguanine may constitute appropriate modified nucleobases. Other suitable nucleobases include 2-thiouracil, 8-bromoadenine, 8-bromoguanine, 2-fluoroadenine, and 2-fluoroguanine. Derivatives of any of the aforementioned modified nucleobases are also appropriate. Substituents of any of the preceding compounds may include $C_1$-$C_{30}$ alkyl, $C_2$-$C_{30}$ alkenyl, $C_2$-$C_{30}$ alkynyl, aryl, aralkyl, heteroaryl, halo, amino, amido, nitro, thio, sulfonyl, carboxyl, alkoxy, alkylcarbonyl, alkoxycarbonyl, and the like.

Descriptions of other types of nucleic acid agents are also available. See, e.g., U.S. Pat. Nos. 4,987,071; 5,116,742; and 5,093,246; Woolf et al. (1992) *Proc Natl Acad Sci USA; Antisense RNA and DNA*, D. A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) *Bioassays* 14:807-15.

Artificial transcription factors can also be used to regulate expression of VEGF or a VEGFR. The artificial transcription factor can be designed or selected from a library, e.g., for ability to bind to a sequence in an endogenous gene encoding VEGF or VEGFR, e.g., in a regulatory region, e.g., the promoter. For example, the artificial transcription factor can be prepared by selection in vitro (e.g., using phage display, U.S. Pat. No. 6,534,261) or in vivo, or by design based on a recognition code (see, e.g., WO 00/42219 and U.S. Pat. No. 6,511,808). See, e.g., Rebar et al. (1996) *Methods Enzymol* 267:129; Greisman and Pabo (1997) *Science* 275:657; Isalan et al. (2001) *Nat. Biotechnol* 19:656; and Wu et al. (1995) *Proc. Natl. Acad. Sci. USA* 92:344 for, among other things, methods for creating libraries of varied zinc finger domains.

Optionally, an artificial transcription factor can be fused to a transcriptional regulatory domain, e.g., an activation domain to activate transcription or a repression domain to repress transcription. In particular, repression domains can be used to decrease expression of endogenous genes encoding VEGF or VEGFR. The artificial transcription factor can itself be encoded by a heterologous nucleic acid that is delivered to a cell or the protein itself can be delivered to a cell (see, e.g., U.S. Pat. No. 6,534,261). The heterologous nucleic acid that includes a sequence encoding the artificial transcription factor can be operably linked to an inducible promoter, e.g., to enable fine control of the level of the artificial transcription factor in the cell, e.g., an endothelial cell.

Administration

An agent described herein may be administered systemically or locally, e.g., topically. Topical administration of an agent described herein is the preferred route of administration. For topical application, the compositions of the present invention can include a medium compatible with a cell, explant or subject. Such topical pharmaceutical compositions can exist in many forms, e.g., in the form of a solution, cream, ointment, gel, lotion, shampoo, soap or aerosol. A wide variety of carrier materials can be employed in the composition of this invention such as alcohols, aloe vera gel, allantoin, glycerin, vitamin A and E oils, mineral oils, and polyethylene glycols. Other additives, e.g., preservatives, fragrance, sunscreen, or other cosmetic ingredients, can be present in the composition.

A preferred vehicle for topical delivery is liposomes. Liposomes can be used to carry and deliver an agent, e.g., a agent described herein, into a cell. Detailed guidance can be found in, e.g., Yarosh et al. (2001) Lancet 357: 926 and Bouwstra et al. (2002) Adv. Drug Deliv. Rev. 54 Suppl 1:S41

For systemic administration the agent may be administered via the orally route or the parenteral route, including subcutaneously, intraperitoneally, intramuscularly, intravenously or other route. For local administration, they are administered topically, transdermally, transmucosally, intranasally or other route. A cell may be contacted extracellularly or intracellularly with the agent, e.g., by microinjection or transfection. The agent may be applied and removed immediately, applied and not removed, and/or repeatedly applied with constant, increasing or decreasing frequency and/or at increasing or decreasing doses or concentrations. More than one route of administration may be used simultaneously, e.g., topical administration in association with oral administration. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well known to those familiar with the art, can be utilized as pharmaceutical excipients for delivery of the pigment modulating composition.

The composition may be provided as, e.g., a cosmetics, a medication or a skin care product. The composition can also be formulated into dosage forms for other routes of administration utilizing conventional methods. A pharmaceutical composition can be formulated, for example, in dosage forms for oral administration as a powder or granule, or in a capsule, a tablet (each including timed release and sustained release formulations), or a gel seal, with optional pharmaceutical carriers suitable for preparing solid compositions, such as vehicles (e.g., starch, glucose, fruit sugar, sucrose, gelatin and the like), lubricants (e.g., magnesium stearate), disintegrators (e.g., starch and crystalline cellulose), and binders (e.g., lactose, mannitol, starch and gum arabic). When the composition is an injection, for example, solvents (e.g., distilled water for injection), stabilizers (e.g., sodium edetate), isotonizing agents (e.g., sodium chloride, glycerin and mannitol), pH-adjusting agents (e.g., hydrochloric acid, citric acid and sodium hydroxide), suspending agents (e.g., methyl cellulose) and the like may be used.

The agent may contain other pharmaceutical ingredients, e.g., a second treatment for skin, e.g., a moisturizer, a sunscreen.

Kits

An agent described herein (e.g., VEGF antibody or an agent that modulates VEGF or VEGFR) can be provided in a kit. The kit includes (a) an agent, e.g., a composition that includes an agent, and (b) informational material. The informational material can be descriptive, instructional, marketing or other material that relates to the methods described herein and/or the use of VEGF or VEGFR for the methods described herein. For example, the informational material relates to acute UVB skin damage, e.g., sunburn.

In one embodiment, the informational material can include instructions to administer an agent described herein in a suitable manner to perform the methods described herein, e.g., in a suitable dose, dosage form, or mode of administration (e.g., a dose, dosage form, or mode of administration described herein). Preferred doses, dosage forms, or modes of administration are topical and percutaneous. In another embodiment, the informational material can include instructions to administer an agent described herein to a suitable subject, e.g., a human, e.g., a human having, or at risk for, acute UVB damage.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about VEGF or VEGFR and/or its use in the methods described herein. Of course, the informational material can also be provided in any combination of formats.

In addition to an agent described herein, the composition of the kit can include other ingredients, such as a solvent or buffer, a stabilizer, a preservative, a fragrance or other cosmetic ingredient, and/or a second agent for treating a condition or disorder described herein. Alternatively, the other ingredients can be included in the kit, but in different compositions or containers than an agent described herein. In such embodiments, the kit can include instructions for admixing an agent described herein and the other ingredients, or for using an agent described herein together with the other ingredients.

An agent described herein can be provided in any form, e.g., liquid, dried or lyophilized form. It is preferred that an agent described herein be substantially pure and/or sterile. When an agent described herein is provided in a liquid solution, the liquid solution preferably is an aqueous solution, with a sterile aqueous solution being preferred. When an agent described herein is provided as a dried form, reconstitution generally is by the addition of a suitable solvent. The solvent, e.g., sterile water or buffer, can optionally be provided in the kit.

The kit can include one or more containers for the composition containing an agent described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an agent described herein. For example, the kit includes a plurality of syringes, ampules, foil packets, or blister packs, each containing a single unit dose of an agent described herein. The containers of the kits can be air tight and/or waterproof.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is a swab.

EXAMPLES

Materials and Methods

UVB-Irradiation Regimen

Female hairless Skh1 mice (8 weeks-old) were exposed to UVB irradiation as described, using a bank of four equally spaced fluorescence lamps (Southern New England Ultraviolet, Bradford, Conn.) (Kochevar et al. (1993) J. Invest. Dermatol. 100:186-93). Mice (n=7 per group) were sham-irradiated or were exposed to UVB irradiation three times a week for 10 weeks with a starting dose of 40 mJ/cm$^2$ (0.5 minimal erythema dose; MED), and gradual increases in increments of 0.5 MED to a maximum dose of 4.5 MED. The total cumulative dose of UVB was 5.46 J/cm$^2$. No acute sunburn reactions were observed. In additional studies, 8-week-old female Skh1 mice, FVB transgenic mice with skin-specific overexpression of murine VEGF164 under control of the K14 promoter (Detmar et al. (1998) J. Invest. Dermatol. 111:1-6) or wild type FVB mice (n=5 per group) were irradiated with a single dose of 40 mJ/cm$^2$ (0.5 MED) or 80 mJ/cm$^2$ (1 MED) of UVB. In addition, wild type mice (n=5/group) were treated with 50 μg of an anti-mouse VEGF neutralizing antibody (R&D Systems, Minneapolis, Minn.) or with 50 μg of control IgG by intraperitoneal injection at 24 hours before exposure to 54 mJ/cm$^2$ of UVB irradiation as described (Hirakawa et al. (2005) Blood 105:2392-9). All animal studies were approved by the Massachusetts General Hospital Subcommittee on Research Animal Care.

Intravital Lymphangiography

Mice (n=7/group) were anesthetized by using avertin (0.4 g/kg, Sigma), and 1 μl of a 1% solution of Evans blue dye in 0.9% NaCl was injected intradermally at the inner surface of the rim of the ear, using a 10 μl Hamilton syringe in order to visualize the lymphatic vessels. Mouse ears were photographed at 1, 3, and 5 minutes after the dye injection.

Quantitative Real-Time RT-PCR

Total cellular RNA was isolated from the whole back skin of mice at 2 days after the last UVB irradiation (n=7/group), using the TRIZOL® reagent (Invitrogen, Carlsbad, Calif.) followed by treatment with RQ1 RNase-free DNase (Promega, Madison, Wis.). The whole skin was homogenized using Tissue Lyser (Qiagen GmbH, Germany) The expression levels of VEGF-A, -C and -D mRNA were investigated by quantitative real-time RT-PCR, using the ABI PRISM® 7000 Sequence Detection System (Applied Biosystems, Foster City, Calif.) as described (Hong et al. (2004) Nat. Genet. 36:683-5). The primers and probes for murine VEGF-A, -C and -D were described previously (Kunstfeld et al. (2004) Blood 104:1048-57). Each reaction was multiplexed with glyceralaldehyde-3-phosphate dehydrogenase (GAPDH) primers (forward 5'-TCACTGGCATGGCCTTCC-3' (SEQ ID NO:1), reverse 5'-GGCGGGCACGTCAGATCCA-3' (SEQ ID NO:2)) and probe (5'-JOE-TTCCTACCCCCAAT-GTGTCCGTCG-TAMRA-3' (SEQ ID NO:3)) as an internal control.

Immunostaining and Computer-Assisted Morphometric Vessel Analysis

Immunofluorescence analyses were performed on 6-µm cryostat sections of mouse tissues, using polyclonal antibodies against murine LYVE-1 (Banerji et al. (1999) J. Cell Biol. 144:789-801), murine CD31 (BD Biosciences, Pharmingen, San Diego, Calif.), and corresponding secondary antibodies labeled with ALEXA FLUOR® 488 or ALEXA FLUOR® 594 (Molecular Probes, Eugene, Oreg.) (Kajiya et al. (2005) EMBO J. 24:2885-95). Sections were examined by a Nikon E-600 microscope (Nikon, Melville, N.Y.) and images were captured with a SPOT™ digital camera (Diagnostic Instruments, Sterling Heights, Mich.). Morphometric analyses were performed using IPLAB™ software (Scanalytics, Fairfax, Va.) as described (Hirakawa et al. (2005) Blood 105: 2392-9). Three different fields of each section were examined and the number of vessels per, square micrometer, the average vessels size and the relative tissue area occupied by lymphatic vessels were determined in the dermis in an area within 200 µm distance from the epidermal-dermal junction. The unpaired Student t-test was used to analyze differences in microvessel density and size. In addition, routine hematoxylin-eosin stains were performed as described previously (Prophet, Arrington, and Sobin (1992) *Laboratory Methods in Histotechnology*).

Example 1

Chronic UVB Irradiation Leads to Enlargement of Cutaneous Lymphatic Vessels

To investigate the effect of UVB irradiation on the lymphatic vasculature, we first performed chronic UVB irradiation of Skh1 hairless mice (Kligman (1996) Clin. Dermatol. 14:183-95) with a cumulative dose of 5.46 J/cm$^2$ over a period of 10 weeks. Chronic UVB irradiation resulted in pronounced wrinkle formation as previously reported (Yano et al. (2002) J. Invest. Dermatol. 118:800-5), whereas no such changes were detected in sham-irradiated mice. Histological examination revealed the typical signs of chronic UVB damage, including epidermal hyperplasia, inflammatory cell infiltration and edema formation (FIGS. 1A and B). Double immunofluorescence stains for the panvascular marker CD31 and for the lymphatic-specific hyaluronan receptor LYVE-1 revealed moderate enlargement of CD31+/LYVE-1− blood vessels (FIGS. 1C and D), in agreement with previous studies (Yano et al. (2005) Br. J. Dermatol. 152:115-21). Surprisingly, LYVE-1-positive cutaneous lymphatic vessels were dramatically increased in size, with irregular shapes and sometimes incomplete endothelial cell lining of the vessel walls, whereas only normal, collapsed lymphatic vessels were found in sham-irradiated mice (FIGS. 1C and D). Computer-assisted morphometric analyses confirmed that the average dermal area occupied by lymphatic vessels (2,5-fold increase over sham-irradiated mice; P<0.01) and the average size of dermal lymphatic vessels (2,1-fold increase; P<0.01) were significantly increased in UVB-irradiated skin, as compared with sham-irradiated mice (FIGS. 1E and F). In contrast, the density of lymphatic vessels was comparable in both groups (FIG. 1G).

Example 2

Figure 2:
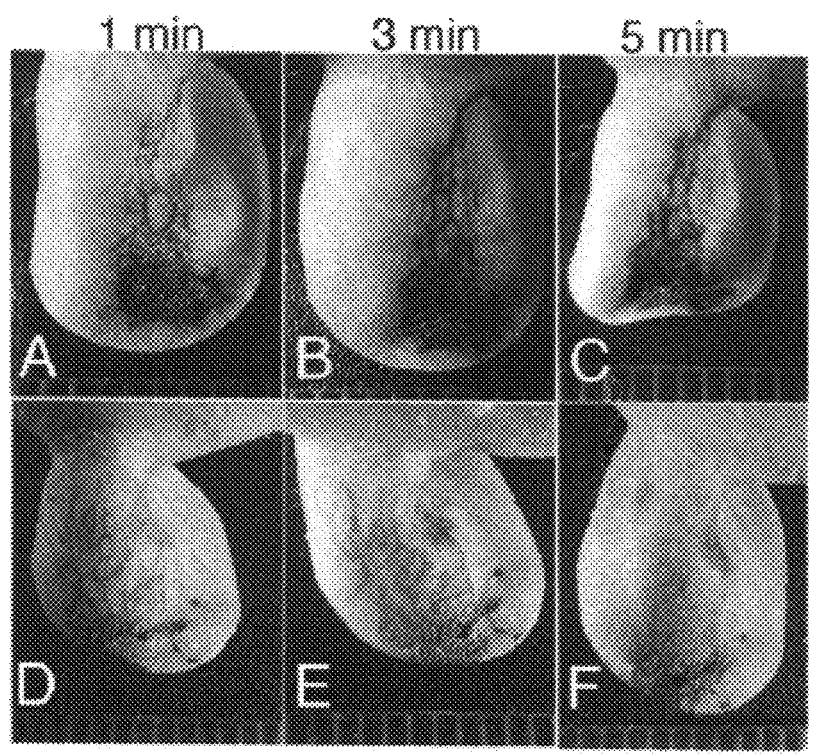
FIGS. 2A-F are photographs of mouse ears with intradermally injected Evans blue dye.

Impaired Function and Increased Leakiness of Lymphatic Vessels after Chronic UVB-Irradiation To further investigate the effects of chronic UVB irradiation on the function of cutaneous lymphatic vessels, Evans blue dye was injected intradermally into the rim of mouse ears. At 1 and 3 minutes after ink injection, markedly dilated lymphatic vessels were visualized in chronically UVB-irradiated mouse skin, as compared with sham-irradiated mice (FIGS. 2A, B, D, E). After 5 minutes, Evans blue dye had extravasated from lymphatic vessels in chronically UVB-irradiated skin, whereas no such leakage was observed in sham-irradiated mice (FIGS. 2C and F). These findings indicate that the enlarged lymphatic vessels after UVB irradiation are leaky and functionally impaired.

Example 3

Figure 3:
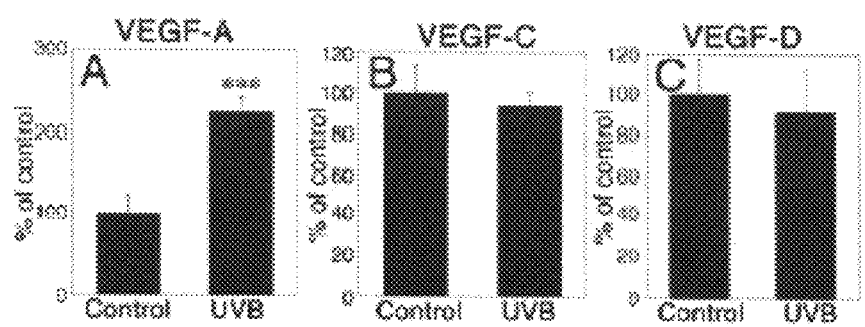
FIGS. 3A-C are bar graphs depicting quantitative real-time RT-PCR analysis of total RNAs isolated from the epidermis of the ear skin at 48 hours after the chronic UVB irradiation. VEGF-A mRNA expression (FIG. 3A) was upregulated in UVB-irradiated epidermis, as compared to sham-irradiated controls (***, P<0.01). In contrast, VEGF-C (FIG. 3B) and VEGF-D (FIG. 3C) mRNA expression levels were comparable in both groups.

Chronic UVB Irradiation Leads to Upregulation of VEGF-A, but not of VEGF-C or -D Expression To investigate whether chronic UVB irradiation resulted in upregulation of any of the known lymphangiogenesis factors, VEGF-A (Nagy et al. (2002) J. Exp. Med. 196:1497-506), VEGF-C or VEGF-D (Jussila et al. (2002) Physiol. Rev. 82:673-700) by epidermal keratinocytes, we next isolated total RNAs from the epidermis of the ear skin, followed by quantitative real-time TAQMAN™ RT-PCR analysis of mRNA expression. We found a 2,2-fold upregulation of VEGF-A mRNA expression in UVB-irradiated epidermis, as compared to sham-irradiated controls (P<0.01; FIG. 3A). In contrast, VEGF-C and VEGF-D mRNA expression levels were comparable in both groups (FIGS. 3B and C). Comparable results were obtained when total RNA isolated from whole skin lysates, including both epidermis and dermis, was examined.

Example 4

Figure 4:
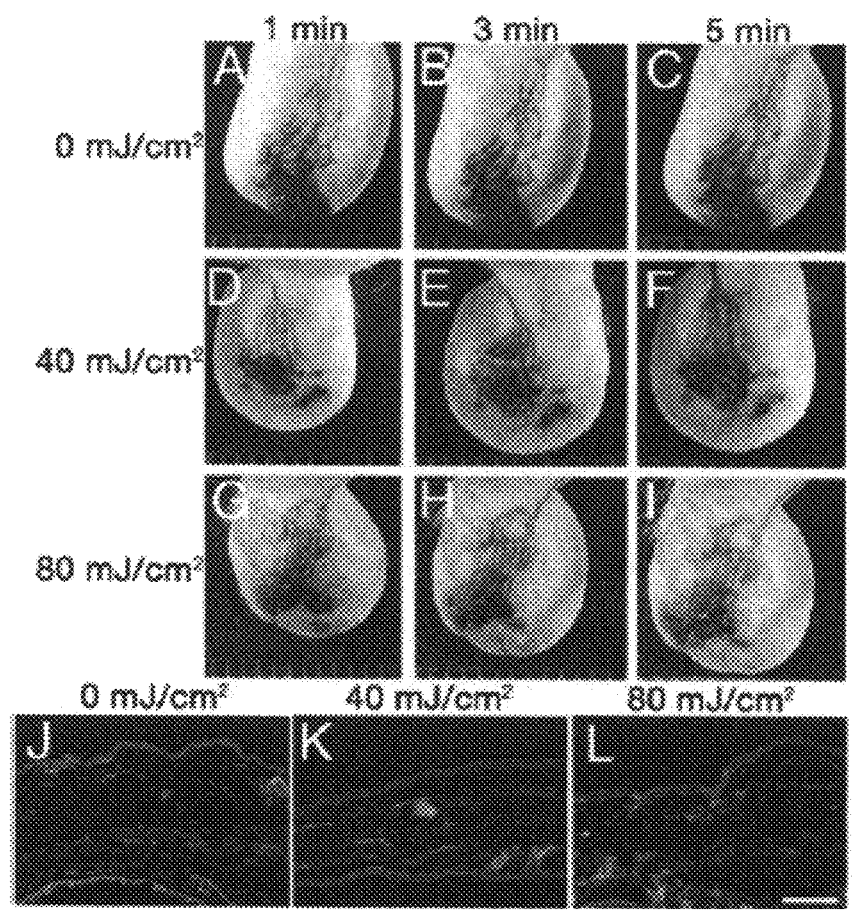
FIGS. 4A-I are photographs of mouse ears with intradermally injected Evans blue dye.
FIGS. 4J-L are immunofluorescence micrographs for CD31 and LYVE-1 in skin samples irradiated with 0 mJ/cm$^2$ (FIG. 4J), 40 mJ/cm$^2$ (FIG. 4K) and 80 mJ/cm$^2$ (FIG. 4L). Differential immunofluorescence analyses of skin sections for LYVE-1 and CD31 revealed marked enlargement of LYVE-1+ lymphatic vessels after UVB irradiation with 80 mJ/cm$^2$ (FIG. 4L). No such changes were observed in non-irradiated skin (FIG. 4J) or in skin irradiated with 40 mJ/cm$^2$ (FIG. 4K). Scale bar: 100 µm.

Acute UVB Irradiation Induces Enlargement and Hyperpermeability of Cutaneous Lymphatic Vessels We next investigated whether a single dose of acute UVB irradiation might be sufficient to impair lymphatic vessel function. Two days after a single dose of 40 mJ/cm$^2$ UVB irradiation (0.5 minimal erythema dose; MED), visualization of cutaneous lymphatic vessels by intradermal Evans blue dye injection revealed that the lymphatic vessels were indistinguishable from those in non-irradiated skin and that they were not hyperpermeable (FIG. 4A-F). In contrast, irradiation with a dose of 80 mJ/cm$^2$ of UVB (1 MED) resulted in enlargement of cutaneous lymphatic vessels (FIG. 4G-H), and pronounced leakiness was observed (FIG. 4I). Differential immunofluorescence analyses of skin sections revealed a dramatic enlargement of LYVE-1+ lymphatic vessels, but only moderate enlargement of CD31+/LYVE-1− blood vessels, after UVB irradiation with 80 mJ/cm$^2$ (FIG. 4L). However, no such changes were observed in non-irradiated skin or in skin irradiated with a UVB dose of 40 mJ/cm$^2$ (FIGS. 4J, K).

Example 5

Figure 5:
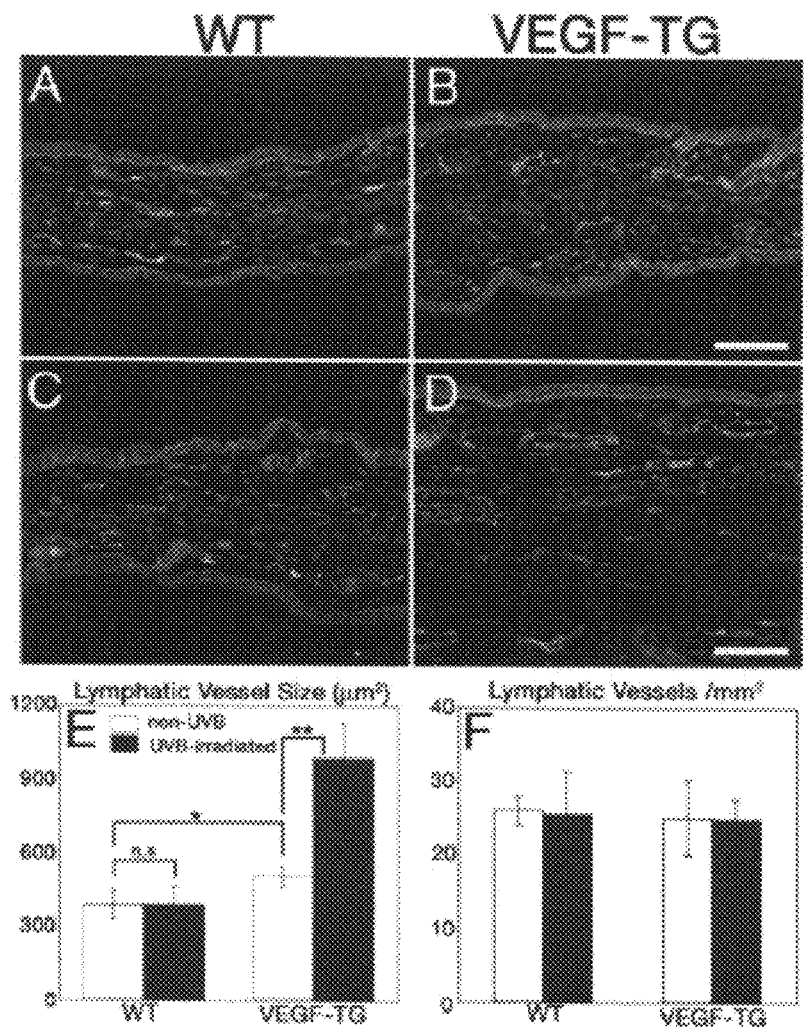
FIGS. 5A-D are immunofluorescence micrographs for CD31 and LYVE-1 in skin samples of wild-type (FIGS. 5A and 5C) and VEGF transgenic (FIGS. 5B and 5D) mice irradiated with a single dose of 40 mJ/cm$^2$ UVB (FIGS. 5C-D) or sham irradiated (FIGS. 5A-B). Sham-irradiated VEGF transgenic mice showed a slight increase in lymphatic vessel size (FIG. 5B), as compared to wild type mice (FIG. 5A). Lymphatic vessels were dramatically enlarged in UVB-irradiated VEGF transgenic mice (FIG. 5D), associated with edema formation. Scale bars: 100 µm.
FIGS. 5E-F are bar graphs depicting morphometric analyses of skin samples from chronic UVB-irradiated and sham irradiated wild-type and VEGF transgenic mice.

Increased Enlargement of Lymphatic Vessels in UVB-Irradiated VEGF-A Transgenic Mice Because we found that the mRNA expression of VEGF-A was up-regulated by epidermal keratinocytes after UVB-irradiation, we next investigated whether epidermis-derived VEGF-A might directly promote the UVB-induced enlargement and leakiness of lymphatic vessels. Therefore, transgenic FVB mice that overexpress murine VEGF164 under control of the keratin 14 promoter (Detmar et al. (1998) J. Invest. Dermatol. 111: 1-6) and FVB wild type mice were exposed to a single dose of 40 mJ/cm$^2$ UVB irradiation or were sham-irradiated. Differential immunofluorescence analyses of ear sections at 2 days after UVB irradiation revealed comparable numbers and sizes of CD31+/LYVE-1- blood vessels and of LYVE-1+ lymphatic vessels in sham-irradiated and UVB-irradiated wild type mice (FIGS. 5A and C). Sham-irradiated VEGF transgenic mice already showed a slight increase in lymphatic vessel size, as compared to wild type mice (FIG. 5B). Importantly, lymphatic vessels were dramatically enlarged after UVB irradiation of VEGF transgenic mice (FIG. 5D), associated with increased ear thickness and edema formation. Computer-assisted morphometric analyses confirmed a 1,3-fold increase of lymphatic vessel size in sham-irradiated VEGF transgenic mice compared to wild type mice ($p<0.05$), and a further, significant 1,9-fold enlargement after UVB irradiation ($p<0.01$; FIG. 5E). The density of lymphatic vessels was comparable in all groups (FIG. 5F).

Example 6

Figure 6:
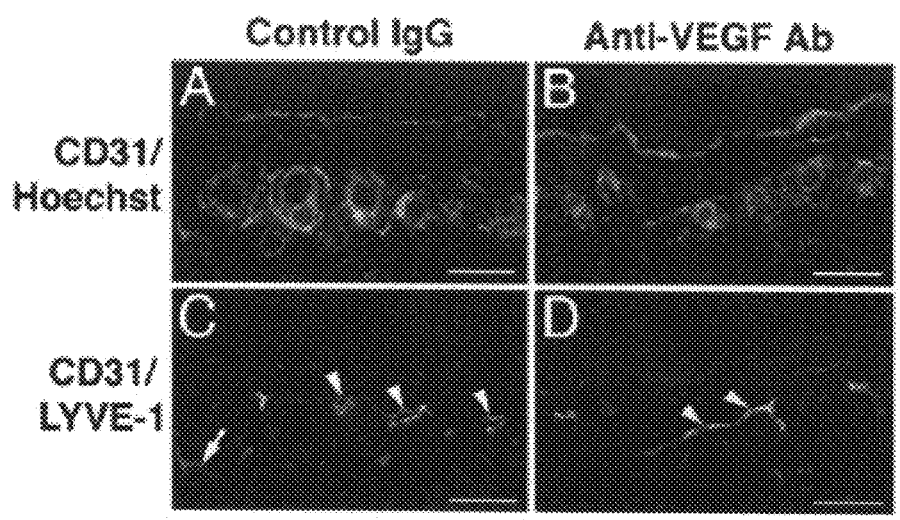
FIGS. 6A-D are immunofluorescence micrographs for CD31 and Hoechst stain (FIGS. 6A-B) or CD31 and LYVE-1 (FIGS. 6C-D) in skin samples mice irradiated with a single dose of 54 mJ/cm$^2$ UVB irradiation one day after intraperitoneal injection of a blocking antibody against VEGF-A (FIGS. 6B and 6D) or of control IgG (FIGS. 6A and 6C). Double immunofluorescence stains for CD31 and LYVE-1 at 2 days after UVB irradiation reveal enlargement of LYVE-1 positive lymphatic vessels (arrow heads), as well as moderate dilation of CD31+/LYVE-1-blood vessels (arrow) in mice treated with control IgG (FIGS. 6A and 6C). Anti-VEGF-A treatment prevented the enlargement of lymphatic and blood vessels (FIGS. 6B and 6D). Scale bars: 100 µm.

Systematic Blockade of VEGF-A Inhibits the UVB-Induced Enlargement of Lymphatic Vessels We next investigated whether systemic blockade of VEGF-A might prevent the UVB-induced lymphatic vessel enlargement. Wild type FVB mice were exposed to a single dose of 54 mJ/cm$^2$ UVB irradiation one day after intraperitoneal injection of a blocking antibody against VEGF-A or of an equal amount of control IgG. Double immunofluorescence stains for CD31 and LYVE-1 at 2 days after UVB irradiation demonstrated pronounced enlargement of LYVE-1 positive lymphatic vessels, as well as moderate dilation of CD31+/LYVE-1-blood vessels in mice treated with control IgG (FIGS. 6A and C). In contrast, systemic treatment with a VEGF-A blocking antibody completely prevented the enlargement of lymphatic and blood vessels (FIGS. 6B and D).

Other Embodiments

A number of embodiments of the invention have been described. Nevertheless, it will be understood that various modifications may be made without departing from the spirit and scope of the invention. Accordingly, other embodiments are within the scope of the following claims.

All cited patents, applications, and references are incorporated herein by reference.

What is claimed is:

1. A method of inhibiting ultraviolet B (UVB)-induced skin damage in a subject, the method comprising:
    administering to the skin of the subject prior to or during UVB light exposure a vascular endothelial growth factor (VEGF)-A antagonist in an amount sufficient to promote lymphatic function in the skin of the subject; and
    administering to the skin of the subject prior to or during UVB light exposure a VEGF-C polypeptide in an amount sufficient to promote lymphatic function in the skin of the subject,
    wherein the promotion of lymphatic function in the skin of the subject inhibits UVB-induced skin damage in the subject.

2. The method of claim 1, wherein the subject is human.

3. The method of claim 1, wherein the VEGF-A antagonist is administered prior to UVB light exposure.

4. The method of claim 1, wherein the VEGF-A antagonist is administered during UVB light exposure.

5. The method of claim 1, wherein the VEGF-C polypeptide is administered prior to UVB light exposure.

6. The method of claim 1, wherein the VEGF-C polypeptide is administered during UVB light exposure.

7. The method of claim 1, wherein the VEGF-A antagonist and the VEGF-C polypeptide are administered prior to UVB light exposure.

8. The method of claim 1, wherein the VEGF-A antagonist and the VEGF-C polypeptide are administered during UVB light exposure.

9. The method of claim 1, wherein the administration of the VEGF-A antagonist is topical, intramuscular, intraperitoneal, subcutaneous, or intravenous administration.

10. The method of claim 1, wherein the administration of the VEGF-C polypeptide is topical, intramuscular, intraperitoneal, subcutaneous, or intravenous administration.

11. The method of claim 1, wherein the VEGF-A antagonist and the VEGF-C polypeptide are administered together in a single composition.

12. The method of claim 11, wherein the composition is administered by topical, intramuscular, intraperitoneal, subcutaneous, or intravenous administration.

13. The method of claim 11, wherein the composition further comprises a moisturizer, a sunscreen, or both.

14. The method of claim 11, wherein the composition is formulated as a solution, cream, ointment, gel, lotion, shampoo, soap, or aerosol.

15. The method of claim 1, wherein the VEGF-A antagonist is administered in a composition comprising the VEGF-A antagonist.

16. The method of claim 15, wherein the composition further comprises a moisturizer, a sunscreen, or both.

17. The method of claim 15, wherein the composition is formulated as a solution, cream, ointment, gel, lotion, shampoo, soap, or aerosol.

18. The method of claim 1, wherein the VEGF-C polypeptide is administered in a composition comprising the VEGF-C polypeptide.

19. The method of claim 18, wherein the composition further comprises a moisturizer, a sunscreen, or both.

20. The method of claim 18, wherein the composition is formulated as a solution, cream, ointment, gel, lotion, shampoo, soap, or aerosol.

* * * * *

UNITED STATES PATENT AND TRADEMARK OFFICE
CERTIFICATE OF CORRECTION

| | | |
|---|---|---|
| PATENT NO. | : 8,367,609 B2 | Page 1 of 1 |
| APPLICATION NO. | : 11/654776 | |
| DATED | : February 5, 2013 | |
| INVENTOR(S) | : Detmar et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 438 days.

Signed and Sealed this
Eighteenth Day of November, 2014

Michelle K. Lee
*Deputy Director of the United States Patent and Trademark Office*